(12) United States Patent
Poulet et al.

(10) Patent No.: US 7,850,978 B2
(45) Date of Patent: *Dec. 14, 2010

(54) VACCINE AGAINST FELINE CALICIVIRUS

(75) Inventors: Hervé Poulet, Sainte Foy-lès-Lyon (FR); Frederic Raymond David, Athens, GA (US)

(73) Assignee: Merial Limited, Duluth, GA (US)

( * ) Notice: Subject to any disclaimer, the term of this patent is extended or adjusted under 35 U.S.C. 154(b) by 281 days.

This patent is subject to a terminal disclaimer.

(21) Appl. No.: 11/040,670

(22) Filed: Jan. 21, 2005

(65) Prior Publication Data

US 2005/0208073 A1    Sep. 22, 2005

Related U.S. Application Data

(60) Continuation-in-part of application No. 10/368,861, filed on Feb. 18, 2003, now Pat. No. 7,029,682, which is a division of application No. 09/616,781, filed on Jul. 14, 2000, now Pat. No. 6,534,066, which is a continuation-in-part of application No. 11/038,682, filed on Jan. 19, 2005.

(60) Provisional application No. 60/193,197, filed on Mar. 30, 2000, provisional application No. 60/537,849, filed on Jan. 21, 2004.

(30) Foreign Application Priority Data

Jul. 16, 1999  (FR) .................................. 99 09420
Feb. 11, 2000  (FR) .................................. 00 01759

(51) Int. Cl.
*C61K 39/12* (2006.01)
*C12Q 1/70* (2006.01)

(52) U.S. Cl. ...................... 424/216.1; 435/5; 424/202.1
(58) Field of Classification Search ....................... None
See application file for complete search history.

(56) References Cited

U.S. PATENT DOCUMENTS

| 3,937,812 | A | 2/1976 | Bittle et al. |
| 5,716,822 | A | 2/1998 | Wardler et al. |
| 6,534,066 | B1 * | 3/2003 | Poulet et al. ............. 424/216.1 |
| 7,029,682 | B2 * | 4/2006 | Poulet et al. ............. 424/216.1 |
| 2006/0160101 | A1 * | 7/2006 | Poulet et al. ................... 435/6 |

FOREIGN PATENT DOCUMENTS

WO    WO 98/56929    12/1988

OTHER PUBLICATIONS

Poulet et al., Database Medline Online, U.S. National Library of Medicine (NLM), "Comparison Between Acute Oral/Respiratory and Chronic Stomatitis/Gingivitis Isolates of Feline Calicivirus: Pathogenicity, Amtigenic Profile and Cross-Neutralization Studies", Archives of Virology (20002) 145 (2) 243-61, XP002138104.
Geissler et al., "Feline Calicivirus Capsid Protein Expression and Capsid Assembly in Cultures Feline Cells". Journal of Virology (1999) vol. 73, No. 1, pp. 834-838.

* cited by examiner

*Primary Examiner*—Zachariah Lucas
*Assistant Examiner*—Agnieszka Boesen
(74) *Attorney, Agent, or Firm*—Judy Jarecki-Black; Chad Kitchen; Merial Limited

(57) ABSTRACT

The present invention relates to improved methods and immunogenic and/or vaccine compositions for providing an immune response to feline calicivirus, including hypervirulent strains of feline calicivirus.

18 Claims, 8 Drawing Sheets

| Isolate/serum | SrA2 | SrF1 | SrG1 | SrH3-2 | SrG3 | SrF30 31 | SrH1-4 | SrI388 b | Sr431 | Sr337 | SrJ5 | SrRMI 1 | SrRMI 2 | SrRMI 3 | SrRMI 5 | SrRMI 6 | SrRMI 7 | SrRMI 9 | Sr255 | SrF9 |
|---|---|---|---|---|---|---|---|---|---|---|---|---|---|---|---|---|---|---|---|---|
| A2 (FR) | 3.5 | 0.8 | 2.5 | 1.2 | 1.0 | 1.8 | 1.3 | 0.7 | 0.8 | 1.1 | 0.9 | 0.7 | 0.7 | 0.7 | 2.0 | 1.2 | 0.7 | 1.7 | 1.2 | 1.8 |
| F1 (FR) | 1.2 | 3.0 | 2.2 | 1.9 | 0.9 | 1.1 | 1.0 | 1.9 | 1.3 | 0.7 | 0.7 | 0.7 | 0.7 | 0.7 | 0.7 | 0.7 | 0.7 | 0.7 | 0.7 | 1.0 |
| G1 (FR) | 1.6 | 0.8 | 2.9 | 1.2 | 1.0 | 1.7 | 0.7 | 0.9 | 2.6 | 0.7 | 0.8 | 0.7 | 0.7 | 0.7 | 0.9 | 0.7 | 0.7 | 0.7 | 1.3 | 1.1 |
| H3-2 (FR) | 0.7 | 0.7 | 0.7 | 2.8 | 0.7 | 0.7 | 0.9 | 0.8 | 1.3 | 0.7 | 1.1 | 1.1 | 0.7 | 0.7 | 0.7 | 0.7 | 0.7 | 0.7 | 0.7 | 0.7 |
| G3 (FR) | 1.0 | 1.1 | 2.4 | 1.7 | 3.5 | 1.6 | 1.3 | 0.9 | 1.8 | 0.7 | 1.1 | 0.7 | 0.7 | 0.7 | 0.7 | 1.0 | 0.7 | 0.7 | 0.8 | 0.7 |
| F3031 (FR) | 2.4 | 1.5 | 2.0 | 1.7 | 1.2 | 3.8 | 1.1 | 1.2 | 2.0 | 0.7 | 1.2 | 0.8 | 0.7 | 0.7 | 0.7 | 1.1 | 0.7 | 1.2 | 1.1 | 2.0 |
| H1-4 (FR) | 0.7 | 0.7 | 1.1 | 1.2 | 0.7 | 0.7 | 3.2 | 0.7 | 1.3 | 0.7 | 1.0 | 2.7 | 0.7 | 0.7 | 0.7 | 1.1 | 0.7 | 0.7 | 0.7 | 0.7 |
| 388b (UK) | 0.7 | 0.7 | 0.7 | 0.7 | 0.7 | 0.7 | 0.7 | 3.3 | 2.1 | 0.7 | 0.9 | 0.7 | 2.3 | 0.7 | 0.7 | 1.3 | 0.7 | 1.8 | 0.7 | 0.7 |
| 431 (UK) | 0.7 | 0.9 | 0.7 | 0.7 | 0.7 | 0.8 | 0.8 | 1.3 | 3.5 | 1.0 | 1.2 | 0.7 | 2.2 | 3.1 | 0.7 | 1.3 | 1.3 | 1.2 | 0.8 | 0.7 |
| 337 (UK) | 1.0 | 1.1 | 1.1 | 0.7 | 0.7 | 0.7 | 1.1 | 1.2 | 2.2 | 3.2 | 3.3 | 2.6 | 2.2 | 0.7 | 0.7 | 1.3 | 1.8 | 0.7 | 0.9 | 0.7 |
| J5 (UK) | 0.7 | 0.7 | 1.0 | 0.7 | 0.7 | 0.7 | 0.7 | 0.8 | 1.6 | 0.7 | 1.0 | 0.8 | 0.7 | 0.7 | 0.8 | 1.3 | 0.7 | 0.7 | 0.9 | 2.0 |
| RMI1 (US) | 0.7 | 0.7 | 1.0 | 1.2 | 0.7 | 0.7 | 0.7 | 1.1 | 1.6 | 0.7 | 1.0 | 2.7 | 0.7 | 0.7 | 0.7 | 1.0 | 1.3 | 0.7 | 0.7 | 0.7 |
| RMI2 (US) | 0.7 | 0.7 | 1.0 | 0.7 | 0.7 | 0.7 | 0.7 | 1.3 | 1.4 | 0.7 | 1.3 | 0.7 | 2.3 | 0.7 | 0.7 | 1.3 | 1.3 | 1.8 | 0.7 | 0.7 |
| RMI3 (US) | 0.7 | 0.7 | 1.2 | 0.7 | 0.7 | 0.7 | 0.7 | 1.3 | 1.5 | 1.8 | 1.0 | 2.6 | 2.2 | 3.1 | 2.0 | 1.3 | 1.8 | 1.2 | 0.7 | 0.7 |
| RMI5 (US) | 1.2 | 0.7 | 1.1 | 0.7 | 0.7 | 0.7 | 0.7 | 1.5 | 1.9 | 0.7 | 0.9 | 0.8 | 2.2 | 0.7 | 2.4 | 1.3 | 0.7 | 0.7 | 0.7 | 0.7 |
| RMI6 (US) | 1.2 | 0.7 | 1.2 | 0.7 | 0.7 | 1.3 | 1.3 | 0.7 | 1.0 | 0.7 | 1.4 | 1.1 | 1.2 | 0.7 | 0.7 | 2.5 | 0.7 | 2.5 | 0.7 | 0.7 |
| RMI7 (US) | 1.1 | 0.7 | 1.1 | 0.7 | 0.7 | 0.7 | 1.3 | 0.7 | 1.8 | 0.7 | 1.2 | 0.7 | 0.7 | 0.7 | 0.8 | 0.7 | 3.0 | 0.7 | 0.7 | 0.7 |
| RMI9 (US) | 1.1 | 0.7 | 1.2 | 0.7 | 0.9 | 0.7 | 0.7 | 0.7 | 1.0 | 0.7 | 1.0 | 0.7 | 0.7 | 0.7 | 0.7 | 2.5 | 0.7 | 2.4 | 0.7 | 0.7 |

FIGURE 1: NEUTRALIZING TITERS OBTAINED DURING CROSS-NEUTRALIZATIONS

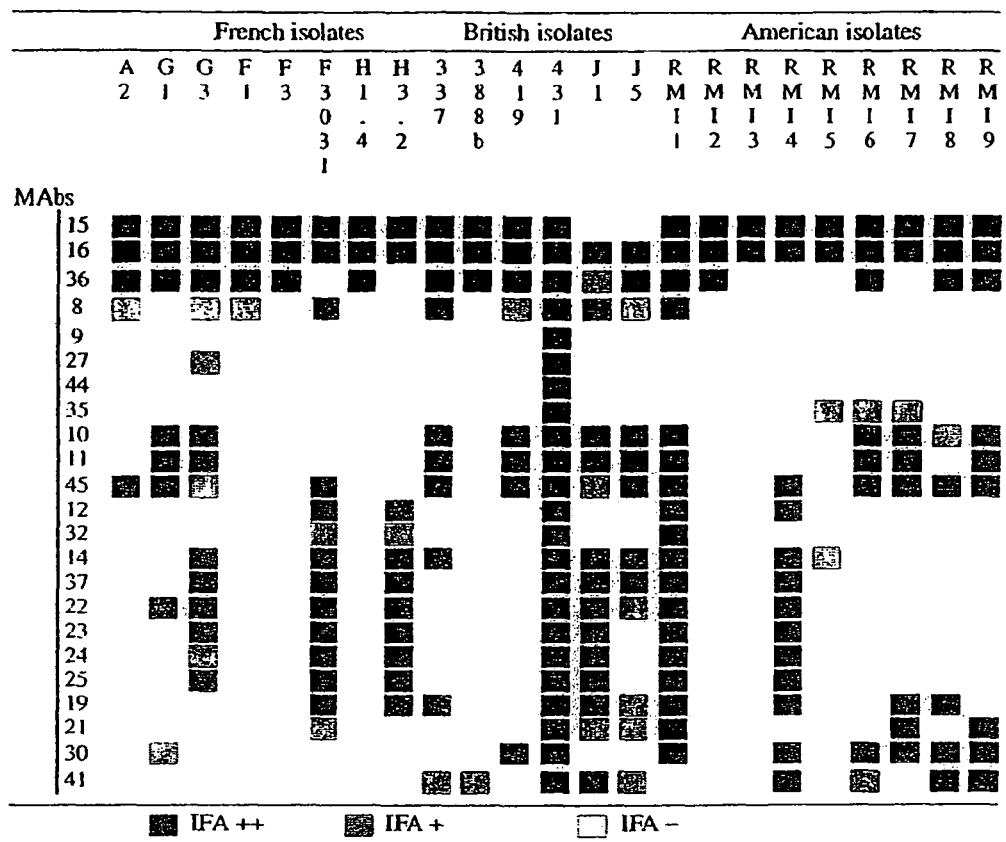
FIGURE 2: IFA PROFILES OF THE ISOLATES BY USING THE ANTI-P66 (FCV431) MONOCLONAL ANTIBODIES

| Group | Cats | General Symptoms | | | | Local Symptoms | | | | | | | Global score |
|---|---|---|---|---|---|---|---|---|---|---|---|---|---|
| | | general body condition | weight | temperature | Total | bucal and nasal ulcer | nasal discharge | ocular discharge | subcutaneous swelling | skin necrosis | skin ulcer | Total | |
| vaccinates | 86623 | 0 | 6 | 4 | 10 | 7 | 6 | 0 | 10 | 0 | 16 | 23 | 33 |
| | 76918 | 0 | 6 | 4 | 10 | 3 | 5 | 3 | 6 | 0 | 14 | 17 | 27 |
| | mean | 0 | 6 | 4 | 10 | 5 | 5.5 | 1.5 | 8 | 0 | 15 | 20 | 30 |
| controls | 84906 | 52 | 4 | 8 | 64 | 19 | 13 | 2 | 10 | 2 | 2 | 46 | 110 |
| | 60758 | 10 | 6 | 5 | 21 | 25 | 20 | 1 | 6 | 0 | 14 | 52 | 73 |
| | mean | 31 | 5 | 6.5 | 42.5 | 22 | 16.5 | 1.5 | 8 | 1 | 8 | 49 | 91.5 |

FIGURE 11

VACCINE AGAINST FELINE CALICIVIRUS

RELATED APPLICATIONS

This application is a continuation-in-part of U.S. application Ser. No. 10/368,861 filed Feb. 18, 2003 now U.S. Pat. No. 7,029,682, which is a divisional of U.S. application Ser. No. 09/616,781, filed on Jul. 14, 2000, now U.S. Pat. No. 6,534,066, which claims priority from French application no. 99 09420, filed Jul. 16, 1999, French application no. 00 01759, filed Feb. 11, 2000, and U.S. provisional application Ser. No. 60/193,197, filed Mar. 30, 2000. This application is also a CIP of application Ser. No. 11/038,682, filed Jan. 19, 2005 which claims priority from U.S. Provisional Patent Application Ser. No. 60/537,849, filed on Jan. 21, 2004.

Each of the foregoing applications, patents and publications, and all documents cited or referenced therein ("application cited documents") and all documents cited or referenced in this specification ("herein cited documents") and all documents referenced or cited in herein cited documents and in application cited documents, including during the prosecution of any of the applications, patents, and application cited documents, are hereby incorporated herein by reference.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

FIELD OF THE INVENTION

The present invention relates to the field of immunology, including diagnostics, assays and vaccines. In particular, the invention relates to the use of particular strains, including hypervirulent strains, of feline caliciviruses for the production of immunogenic compositions and of vaccines, in particular inactivated or subunit vaccines, against feline calicivirosis. The use of these particular strains, including hypervirulent strains, in immunogenic compositions and vaccines provides a superior immune response that provides protection against multiple strains of feline caliciviruses. These immunogenic compositions and these vaccines may also be combined with immunogenic compositions or vaccines prepared on the basis of other feline pathogens, for the production of multivalent immunogenic compositions and vaccines. The present invention additionally relates to diagnostic tests for determining infection with a strain of feline calicivirus, as well as assays for determining the presence or absence of feline calicivirus proteins and/or antigens.

BACKGROUND

Feline caliciviruses (FCV) were first described in 1957 (Fastier, 1957). Feline caliciviruses and feline herpesviruses are the two principal sources of viral diseases of the upper respiratory tract in cats. The FCV viruses affect a large number of animals, with FCV carrying infection rates of the order of 15 to 25%, and an anti-FCV seroprevalence of 70 to 100% (Coutts, 1994; Ellis, 1981; Harbour, 1991; Reubel, 1992). After an initial phase of hyperthermia, these respiratory diseases are generally accompanied by buccal ulcerations on the palate, tongue, lips, and/or nose, rhinitis, chronic stomatitis, conjunctivitis, and possibly anorexia and asthenia. The FCV viruses can also cause pneumonia, enteritis, and articular pain, also known as lameness syndrome.

In general, FCV can be isolated from 15 to 25% of the overall cat population (Harbour, 1991), 45 to 60% of cats with upper respiratory tract infection (Harbour, 1991; Reubel, 1992) and 50 to 92% of cats with chronic stomatitis (Knowles, 1989; Harbour, 1991).

The FCV virus is only transmitted horizontally; to date, there are no known cases of vertical transmission from the mother to its kitten during gestation (Johnson, 1984). Instead, FCV is transmitted by contact between infected animals and healthy animals or through exposure to droplets in the air as occurs through sneezing (Wardley, 1976).

Feline calicivirus of the Caliciviridae familly is a non-enveloped virus, comprising a single-stranded positive-sense RNA genome that is polyadenylated and is about 7.7 kilobases in size (Radford, 1997). The FCV capsid is comprised of a single major capsidal protein of 66 kDa (kilodalton), the p66 protein. A review of the molecular biology of the caliciviruses can be found in Clarke and Lambden.

Like many RNA viruses, a large heterogeneity exists within the viral population of FCV. The antigenic variations, demonstrated since the beginning of the 1970s by cross-serum neutralization experiments, make it possible to classify the FCVs into several viral strains or quasispecies (Radford, 1997).

Several FCV strains have been identified and isolated, in particular strain F9 (deposited with the American Type Culture Collection or ATCC under the accession number VR-782), strain 2280 (ATCC VR-2057), strain KCD (ATCC VR-651) and strain CFI (ATCC VR-654).

Vaccination against FCV was introduced at the end of the 1970s using attenuated FCV strains, mainly strain F9 which was isolated in the United States in 1958 (Bittle, 1960) or those strains derived from F9 by passage in vitro or in vivo ("F9-like"). These attenuated vaccines comprises the majority of the commercial FCV vaccines available.

Inactivated vaccines are also commercially available, and all of these inactivated vaccines contain an adjuvant. These inactivated vaccines mainly use strains 255 and 2280, which were isolated in the United States in 1970 in a cat with a pneumonia (Kahn and Gillepsie, 1970; Povey, 1980) and in 1983 in a cat suffering from lameness (Pedersen, 1983; Pedersen and Hawkins, 1995), respectively.

Inactivation of FCV for use in vaccines may be accomplished by a variety of methods, including the use of formalin. For example, Povey describes a formalin inactivated and adjuvanted FCV preparation used in kittens (Povey, 1978).

U.S. Pat. No. 6,534,066 describes the use of new strains of FCV for the production of FCV vaccines. When the vaccine is an inactivated one, the inactivation occurs through chemical means (e.g. formalin, or formaldehyde, β-propiolactone, ethylenimine, binary ethyleneimine) and/or a heat treatment. Preferably, the virus is inactivated by ethyleneimine. The vaccines are preferably adjuvanted, for example with an oil-in-water emulsion as described in example 8 of the patent.

U.S. Pat. No. 6,355,246 describes both attenuated and inactivated FCV vaccines that preferably comprise an adjuvant. In this patent, inactivation is accomplished through the use of formaldehyde or binary ethyleneimine (BEI).

As mentioned previously, the inactivated vaccines typically contain an adjuvant to improve the immune response and to induce a better protection against heterologous FCV strains emerging in the cat population. However, adjuvanted vaccines induce a higher rate of local adverse reactions than non-adjuvanted ones (Gobar, 2002) and thereby increase the risk of vaccine-associated fibrosarcomas at the injection site (Baker, 1998).

Non-adjuvanted FCV vaccines are typically modified live vaccines usually containing the F9 strains as described above. The residual virulence of FCV F9 has been incriminated by several authors in post-vaccinal calicivirosis (reversion to virulence) (Dawson, 1993). FCV modified live strains are implicated in the emergence of new antigenic variants in the field (Radford, 1997). Therefore, the safety of modified live vaccines is questionable.

Although only one FCV serotype exists, antigenic variation between FCV isolates is observed and new field isolates are regularly identified (Lauritzen, 1997).

Accordingly, because of antigenic drift over time, antisera produced against vaccine strains isolated in the 1960-70s, including strains such as F9, 255 or 2280, neutralize only a few isolates of those calicivirus strains prevalent in the 1990s and 2000s. For example, the anti-F9 serum neutralizes 43% of the American isolates of the period 1990-1996, compared to 56% of the isolates for the period 1980-89 and 86% of the isolates for the period 1958-79, and only 10% of the English isolates of the period 1990-96 (Lauritzen, 1997). Therefore, attenuated and inactivated vaccines from old FCV strains no longer offer sufficient protection against recent FCV strains.

Despite the use of vaccination against FCV since the end of the 1970s, FCV-associated diseases continues to be a significant clinical problem. And, as described previously, new hypervirulent strains have recently arisen. Several mechanisms explain the persistence of FCV infection and FCV-related diseases in face of vaccination, including the lack of broad cross protection afforded by vaccinal strains due to the evolution of the FCV population under the immune pressure induced by vaccination (Geissler, 1997); vaccinal strains from attenuated vaccines may contribute to acute and chronic FCV infection (Dawson, 1993; Pedersen, 1995; Radford, 1997); both inactivated and live vaccines protect the cat against clinical disease but not against infection (Pedersen, 1995); and, FCV is able to evolve and escape from immune pressure by giving rise to mutants which are more vaccine resistant (Knowles, 1990; Johnson, 1992).

As a result, the current calicivirus vaccines must be replaced by vaccines that are more adapted to the current epidemiological situation and which provide greater cross-neutralization against the isolates currently identified in the feline populations. A promising vaccine would be one that is either inactivated or recombinant and which is based on a newer strain of FCV. Recently, outbreaks of a very severe calicivirosis have been noted in the United States and other countries. One of these hypervirulent and immunodominant strains has been selected as vaccine candidate and is described herein as an alternative to the traditional FCV vaccines.

Furthermore, in cats an additional problem arising from FCV vaccination is the presence of inflammation at the injection site, often as the result of the presence of an adjuvant in the vaccine, which may be a factor in post-vaccinal fibrosarcomas. Therefore, local tolerance of the vaccine is of strategic importance, and should be considered when developing new vaccines such that the ideal vaccine must be free of adjuvant and have an excellent local tolerance.

Accordingly, the present invention seeks to address those problems evident in the traditional vaccines by utilizing a recent strain representative of the FCV population in an inactivated or recombinant vaccine (as opposed to a modified live vaccine) (Pedersen, 1995) that has improved local tolerance of the vaccine, and the FCV strain used in the vaccine must be broadly cross-protective—alternatively, the inclusion of several strains has been previously proposed (Baulch-Brown, 1997; Dawson, 1993; Knowles, 1990).

OBJECT OF THE INVENTION

An objective of the present invention is the detection of new FCV strains which induce antibodies in felines having a broad cross-neutralization spectrum.

Another objective of the invention is the production of immunogenic compositions and/or vaccines against feline calicivirosis from these FCV strains. A further objective of the invention includes methods of providing an immune response comprising administration of said immunogenic compositions and/or vaccines.

Yet another objective of the invention is the production of multivalent immunogenic compositions and/or multivalent vaccines against feline calicivirosis and against at least one other feline pathogen, as well as methods of providing an immune response comprising administeration of said multivalent immunogenic compositions and/or multivalent vaccines.

A further objective of the present invention is the production of the aforementioned compositions and/or vaccines against feline calicivirosis and/or multivalent immunogenic compositions and/or vaccines wherein the composition and/or vaccine is non-adjuvanted. For example, one objective of the present application involves subjecting FCV to a formaldehyde treatment and/or treatment with an inactivating agent prior to preparation of the composition and/or vaccine. Accordingly, an object of the present invention is production of a non-adjuvanted inactivated FCV immunogenic composition or vaccine comprising FCV that has been inactivated by an inactivating agent and stabilized by an aldehyde compound formed of a linear alkyl C1-C5 chain comprising one aldehyde group when the chain is C1 and two terminal aldehyde groups when the chain is C2-C5, and optionally one aldehyde group may be replaced by a cetone or an epoxy group when the chain is the C2-C5 chain, and the immunogenic composition or vaccine is either in freeze-dried form or in a liquid form in a veterinarily acceptable excipient or vehicle.

Still another object of the invention is a method of immunization of an animal of the felidae family, preferably a cat, including new born, kitten, male, female, pregnant female, against feline calicivirosis, comprising the administration of a non-adjuvanted inactivated and stabilized FCV immunogenic composition or vaccine according to the invention; or against at least two feline diseases including FCV, comprising the administration of a non-adjuvanted combined vaccine containing inactivated and stabilized FCV according to the invention, and at least one immunogen from another feline pathogen or recombinant vector that expresses at least one immunogen from another feline pathogen.

These and other embodiments are disclosed or are obvious from and encompassed by, the following Detailed Description.

BRIEF DESCRIPTION OF THE DRAWINGS

The following Detailed Description, given by way of example, and not intended to limit the invention to specific embodiments described, may be understood in conjunction with the accompanying Figures, in which:

FIG. 1: shows neutralizing titers obtained during cross-neutralizations as described in Example 4;

FIG. 2 shows IFA profiles of isolates by using ant-p66 (FCV431) monoclonal antibodies; monoclonal antibody 44 is specific to FCV 431.

FIG. 11 is a chart depicting the clinical scores of vaccinated and control animals following challenge with FCV 100869.

DETAILED DESCRIPTION

Figure 3:
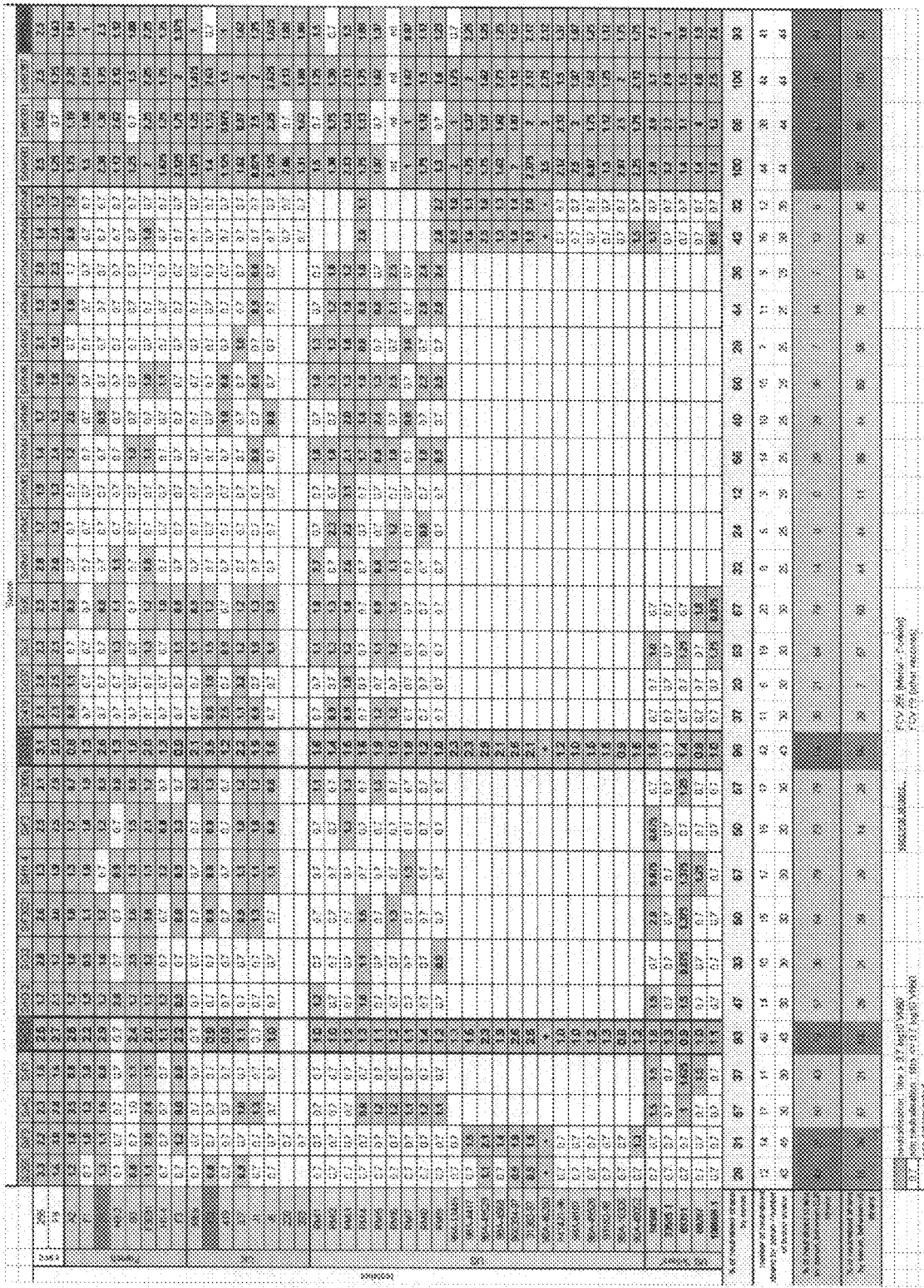
FIG. 3 shows neutralizing titers obtained during cross-neutralizations as described in Example 10.
Figure 4:
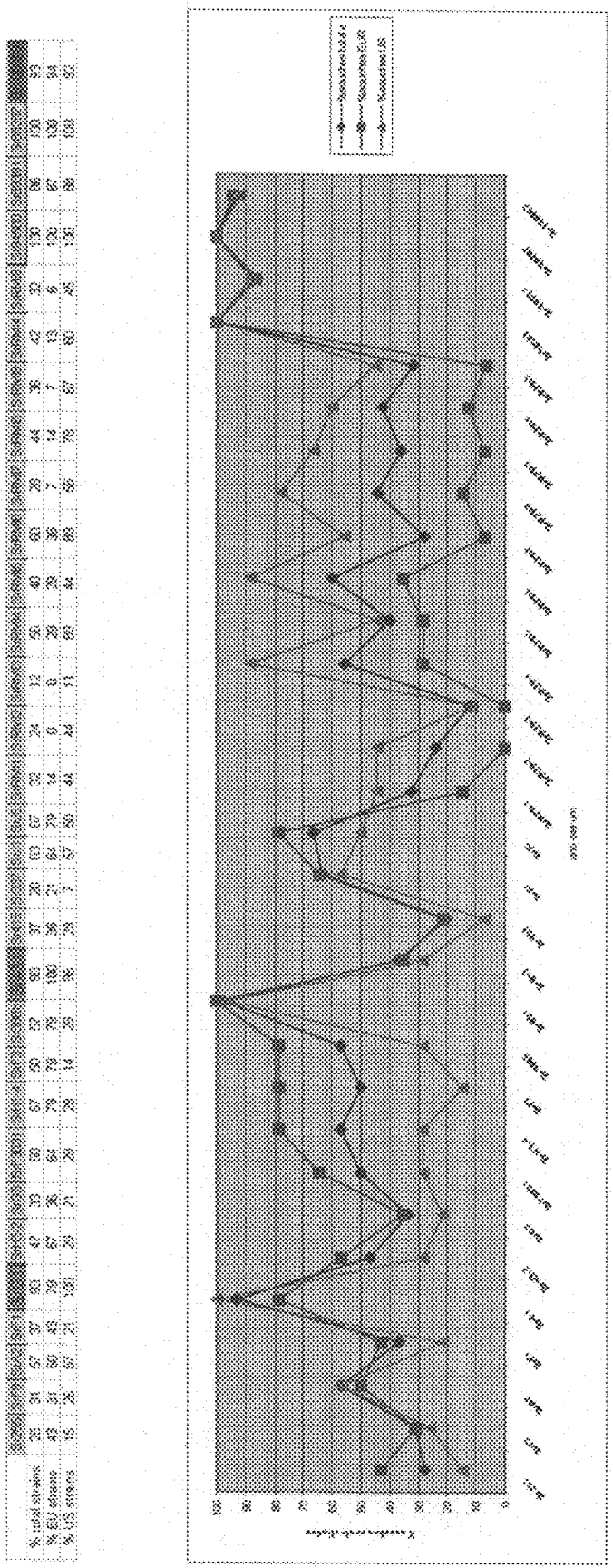
FIG. 4 shows the percent of heterologous isolates seroneutralized by each strain of FCV in both chart and graph form.

In one aspect, the present invention provides an antigenic, immunological or vaccine composition or a therapeutic composition for inducing an antigenic or immunological response in a host animal inoculated with the composition, wherein the antigenic or immunological response is against FCV infection. Accordingly, the present invention provides an improved antigenic, immunological or vaccine composition or a therapeutic composition against FCV. The present invention differs from traditional FCV vaccines by the type of FCV strain used and by the fact that the present invention is advantageously inactivated and not modified live.

As used herein, an "antigen" is a substance that is recognized by the immune system and induces an immune response. A similar term used in this context is "immunogen".

As also used herein, the term "immunogenic composition" covers any preparation capable, once administered to cats, of inducing an immune response directed against the feline pathogen considered. "Vaccine" is understood to mean a preparation capable of inducing effective protection.

In one aspect of the present invention, there is provided an antigenic, immunological or vaccine composition or a therapeutic composition which is prepared from feline calicivirus strain 431, or an equivalent thereto, advantageously in inactivated or subunit form, in a veterinarily acceptable vehicle or excipient. In another aspect of the present invention, there is provided an antigenic, immunological or vaccine composition or a therapeutic composition which is prepared from feline calicivirus strains 431 and G1, or equivalent thereto, advantageously in inactivated or subunit form, in a veterinarily acceptable vehicle or excipient. In a further aspect of the present invention, there is provided an antigenic, immunological or vaccine composition or a therapeutic composition which is prepared from one or more of feline calicivirus strain 100869, 94580, 33585-1, 89391, or 88287, or an equivalent thereto, advantageously in inactivated or subunit form, in a veterinarily acceptable vehicle or excipient. In a further aspect of the present invention, there is provided an antigenic, immunological or vaccine composition or a therapeutic composition which is prepared from at least one feline calicivirus strain elicits cross-neutralization, advantageously in inactivated or subunit form, in a veterinarily acceptable vehicle or excipient.

Preferably, the FCV strain(s) is/are selected from those recently isolated from the field. Preferred strains include the strains FCV 431 (deposited at the CNCM Collection Nationale de Cultures de Microorganismes, Pasteur Institute, 25 Rue du Docteur Roux F-75724 Paris Cedex 15, France, "CNCM") under the accession number I-2166 on Mar. 12, 1999; or any strain reacting with the monoclonal antibody 44 secreted by the hybridoma deposited at the CNCM under the accession number I-2282; (see U.S. Pat. No. 6,534,066), FCV G1 (deposited at the CNCM) under the accession number I-2167 on Mar. 12, 1999. Additional preferred strains include FCV RMI6, deposited at the American Type Culture Collection (10801 University Boulevard Manassas, 20110-2209VA, USA; "ATCC") under the accession number PTA-10108 on Jun. 3, 2009; FCV RMI9, deposited at the ATCC under the accession number PTA-10109 on Jun. 3, 2009; FCV 94580, deposited at the ATCC under the accession number PTA-10105 on Jun. 3, 2009; FCV 33585, deposited at the ATCC under the accession number PTA-10106 on Jun. 3, 2009; FCV 89391, deposited at the ATCC under the accession number PTA-10107 on Jun. 3, 2009; and FCV 88287, deposited at the ATCC under the accession number PTA-10104 on Jun. 3, 2009. A final preferred viral strain FCV 100869 deposited at the ATCC under the accession number PTA 5930 on 22 Apr. 2004 and more generally the new highly virulent strains described in publications (Pedersen et al. Vet. Microbiol. 2000.73. 281-300; Schorr-Evans et al. JFMS. 2003.5.217-226; Hurley et al. Vet. Clin. Small Anim. 2003.33. 759-772).

It is generally considered that an FCV strain seroneutralizes another FCV strain when the heterologous serum neutralization titer is greater than or equal to $1.2 \log_{10} VN_{50}$ (Povey C. and Ingersoll J., Infection and Immunity, 1975, 11, 877-885). This value is used herein as the positivity threshold. However, the cross-serum neutralization results obtained with an FCV isolate having a homologous serum neutralization titer of less than or equal to $2 \log_{10} VN_{50}$ cannot be interpreted.

A second method for establishing the equivalence of an FCV strain with respect to the FCV 431 strain is to use monoclonal antibodies specific for the FCV 431 strain and to test the candidate FCV strain by indirect immunofluroescence (IIF). The Applicant has thus succeeded in producing several monoclonal antibodies which have proved specific for the 431 strain, one of which is monoclonal antibody 44. There is equivalence if there is reactivity in immunofluorescence with monoclonal antibodies specific for 431, for example with the monoclonal antibody 44. This monoclonal antibody and the corresponding hybridoma are available from the Applicant upon simple request and are also disclosed in the article by Poulet et al. Arch. Virol. 2000. 145. 1-19. The corresponding hybridoma was also deposited on 11 Aug. 1999 under the terms of the Budapest Treaty at the CNCM under the accession number I-2282. It goes without saying, however, that persons skilled in the art are perfectly capable of producing monoclonal antibodies by conventional techniques and of selecting, relative to the panel, those which are specific for the 431 strain.

Those strains identified as equivalent to 431 herein were identified during cross-serum neutralization tests between the 18 FCV isolates of the reference panel of Example 4, wherein it was found, surprisingly, that the antiserum for isolate 431 neutralizes 14 of the 17 heterologous isolates of the reference panel (the homologous serum neutralization titer is not taken into account). By comparison, the antisera for the "historical" vaccine strains 255 and F9 neutralize only 2 of the 18 panel isolates each.

Unexpectedly, the Applicant has therefore found with the FCV 431 strain a dominant strain which can be used for the protection of Felidae and in particular of cats against most FCV strains. By virtue of the panel of FCV strains disclosed here, it is possible for persons skilled in the art to select other dominant FCV strains. By way of equivalence, the invention also covers through the FCV 431 strain the FCV strains which are equivalent thereto, which have antibodies with broad cross-neutralization spectrum.

Equivalence therefore exists when the antiserum for an FCV strain seroneutralizes at least 13 of the 18 heterologous isolates of the reference panel (that is to say including FCV 431), preferably when it seroneutralizes at least 14 of the 18 heterologous isolates of the reference panel, still more preferably when it seroneutralizes at least 15 of the 18 heterologous isolates of the reference panel.

Additionally, applicants have also found that FCV 100869 and other hypervirulent strains are dominant strains which can be used for the protection of Felidae and in particular of cats against most FCV strains.

As used herein, the term "hypervirulent" is understood as having the definition attributed to it in the art, specifically, a hypervirulent strain shows a marked increase in virulence over traditional strains. Accordingly, as used herein, for example, strain 100869 has an increased virulence over older strains such as 431 and 255 and F9.

Similarly, equivalents of FCV strains such as 100869 may be determined by identifying those strains which also seroneutralize at least 41 of the 44 heterologous isolates of the reference panel of Example 10, preferably at least 42 of the 44 heterologous isolates, or at least 43 of the 44 heterologous isolates or 44 of the 44 heterologous isolates of the reference panel. Furthermore, one of skill in the art may identify equivalents of any of the strains 100869, 94580, 33585-1, 89391, or 88287 identified herein through other techniques described herein or known to those of skill in the art without undue experimentation.

Another embodiment of the present invention is therefore immunogenic compositions and vaccines comprising, in addition to the antigens of the FCV 431 strain or one of its equivalents according to the invention, antigens of at least one other FCV strain, especially a complementary strain, in particular chosen from the group comprising G1, RMI6, RMI9, which includes their equivalents, in a veterinarily acceptable vehicle or excipient, and optionally an adjuvant. Preferably, the antigens obtained from the other FCV strain(s) comprise inactivated virus or subunits.

The FCV G1, RMI6 and RMI9 strains were chosen for their complementarity to the FCV 431 strain, namely that the combination of the antisera for 431 and for one of these three FCVs seroneutralize 100% of the isolates of the reference panel, that is to say that these three FCV strains have a homologous serum neutralization titer greater than or equal to 2 $\log_{10}$ VN$_{50}$ and heterologous serum neutralization titers greater than or equal to 1.2 $\log_{10}$ VN$_{50}$ with respect to the FCV isolates of the reference panel against which the 431 antiserum does not seroneutralize or seroneutralizes weakly (value less than 1.2 $\log_{10}$ VN$_{50}$). The invention also covers the equivalent FCV strains having the same complementarity with respect to the FCV 431 strain. It is also possible to produce and select monoclonal antibodies specific for these strains, in particular for G1, which makes it possible to determine equivalents on this other basis.

Another aspect of the invention is in particular the combination of the two FCV 431 and G1 strains for the production of immunogenic compositions or of inactivated or subunit vaccines.

Surprisingly, the combination of the two FCV G1 and 431 strains causes advantageously a synergistic effect. During studies on the complementarity of the FCV G1 and 431 strains, the immune responses induced by G1 alone, 431 alone or the combination of both (G1+431) were compared. The group of animals which were immunized with the combination of the two FCV G1 and 431 strains had the benefit of a better clinical protection. Indeed, one embodiment of the present invention is the use of FCV 431 in combination with FCV G1 in the preparation of a composition to induce an immune response against hypervirulent strains of FCV, including those strains identified herein, and in particular strain 100869. Similarly, another embodiment of the present invention is immunogenic and vaccine compositions comprising GCV 341 in combination with FCV G1 or equivalents thereto which can be used for the protection of the Felidae and in particular of cats against most FCV strains, including hypervirulent strains of FCV, including those identified herein, and in particular strain 100869.

Another embodiment of the present invention is a multivalent vaccine comprising at least one inactivated feline calicivirus valency, comprising at least the FCV 431 strain, which includes its equivalents, and optionally at least one other FCV strain, in particular a strain which is complementary within the meaning of the invention, in particular chosen from G1, RMI6 and RMI9, and at least one valency for another feline pathogen, in a veterinarily acceptable vehicle or excipient and preferably with an adjuvant, in particular one of those described above. It is likewise possible to produce subunit-based multivalent vaccines.

Said feline pathogens are in particular chosen from the group comprising the feline rhinotracheitis virus or the feline herpesvirus (FHV), the feline leukemia virus (FeLV), feline panleukopenia virus or feline parvovirus (FPV), the feline infectious peritonitis virus (FIPV), the feline immunodeficiency virus (FIV), the rabies virus, *Chlamydia* (e.g., *Chylamydophila felis*).

Preferably said vaccines combine vaccinal components for:
FCV, FHV, FPV, FeLV and *Chlamydia*
FCV, FHV, FPV and FeLV
FCV, FHV, FPV and Rabies
FCV, FHV, FPV and *Chlamydia*
FCV, FHV, FPV, *Chlamydia* and Rabies
FCV, FHV and FPV
FCV, FHV and *Chlamydia*
FCV and FHV.

In a preferred embodiment of these various combinations, attenuated live micro-organisms are used for FHV, FPV and *Chlamydia* and a recombinant vector(s) expressing FeLV genes is/are used for FeLV. The recombinant vector may be a canarypox virus (for example vCP97 as described in U.S. Pat. No. 5,753,103) that expresses env and gag/pol FeLV genes.

Another object of the invention is thus a non-adjuvanted combined immunogenic composition or vaccine comprising one stabilized and inactivated FCV and at least one vaccinal component for inducing in the host an immune response against at least one other feline pathogen, wherein said component may be an immunogen from another feline pathogen or a recombinant vector expressing this immunogen, wherein the non-adjuvanted combined immunogenic composition or vaccine is either in a freeze-dried form or in a liquid form in a veterinarily acceptable vehicle or excipient. The freeze-dried form is preferred.

In a preferred embodiment, the non-adjuvanted combined immunogenic composition or vaccine comprises either the vaccinal component in the form of a live attenuated micro-organism or of a recombinant vector expressing at least one immunogen from the feline pathogen. The recombinant vector may be a plasmid or a viral vector; for example the vector is a poxvirus, an adenovirus, or a herpesvirus. The freeze-dried form is again preferred.

In accordance with a feature of the invention, it is possible to produce immunogenic compositions or subunit vaccines, by extraction of the capsid from the virus, with optionally inactivation before or after the extraction. These preparations and vaccines therefore comprise, as sole active ingredient or otherwise, such a product of extraction containing predominantly capsid protein and optionally subfragments, optionally inactivated, produced from the strains according to the invention, in particular strain 431, which includes its equivalents, optionally also from another FCV strain, in particular G1 or equivalents. These subunit vaccines and preparations are advantageously supplemented with adjuvant, for example as described supra. It is also possible to mix whole inactivated vaccine or preparation and subunit vaccine or preparation.

The subject of the invention is also an immunogenic composition or a vaccine based on the G1 strain, in particular which is inactivated or a subunit of extraction.

The culture and propagation of the FCV viruses is preferably carried out on feline cells, more particularly on Crandell-Reese Feline Kidney or CRFK cells (accessible from the American Type Culture Collection under the number CCL-94) with a multiplicity of infection (moi) of 2 to 0.01 cell culture infectious doses 50% ($CCID_{50}$) per cell, preferably 0.5 $CCID_{50}$/cell.

After harvesting and clarifying, the FCV viruses intended to produce an inactivated immunogenic composition or an inactivated vaccine are inactivated by a chemical treatment (e.g. formalin or formaldehyde, β-propiolactone, ethylenimine, binary ethylenimine (BEI)) and/or a heat treatment. Preferably, the viruses according to the invention are inactivated by the action of ethylenimine formed immediately before use from bromoethylamine (BEA). The viral particles may be concentrated by conventional concentration techniques, in particular by ultrafiltration and then optionally purified by conventional purification means, in particular gel filtration techniques or selective precipitation techniques in particular in the presence of polyethylene glycol (PEG). A purification without previous concentration can also be done.

For the production of an immunogenic composition or of an inactivated or subunit vaccine, the viral particles are taken up in a veterinarily acceptable vehicle or excipient, and optionally supplemented with an adjuvant. The quantity of antigen is in particular equal to a preinactivation titer of about $10^5$ to about $10^{10}$ $CCID_{50}$ per dose, preferably of about $10^8$ to about $10^9$ $CCID_{50}$ per dose. Such an administration enables a systemic immune response, or humoral or cell-mediated responses.

The inventive FCV compositions, can be prepared in accordance with standard techniques well known to those skilled in the pharmaceutical or veterinary art. Such compositions can be administered in dosages and by techniques well known to those skilled in the medical or veterinary arts taking into consideration such factors as the age, sex, weight, species and condition of the particular patient, and the route of administration. The compositions can be administered alone, or can be co-administered or sequentially administered with compositions, e.g., with "other" immunological composition, or attenuated, inactivated, recombinant vaccine or therapeutic compositions thereby providing multivalent or "cocktail" or combination compositions of the invention and methods employing them. The composition may contain combinations of the FCV component and one or more unrelated feline pathogen vaccines (e.g., epitope(s) of interest, antigen(s) and/or vector or virus such as a recombinant virus. Again, the ingredients and manner (sequential or co-administration) of administration, as well as dosages can be determined taking into consideration such factors as the age, sex, weight, species, and, the route of administration.

Examples of compositions of the invention include liquid preparations for mucosal administration, e.g., oral, nasal, ocular, etc., administration such as suspensions and, preparations for parenteral, subcutaneous, intradermal, intramuscular (e.g., injectable administration) such as sterile suspensions or emulsions. In such compositions the FCV may be in admixture with a suitable carrier, diluent, or excipient such as sterile water, physiological saline, or the like. The compositions can also be lyophilized. The compositions can contain auxiliary substances such as wetting or emulsifying agents, pH buffering agents, adjuvants, preservatives, and the like, depending upon the route of administration and the preparation desired.

To supplement the immunogenic compositions and vaccines according to the invention with adjuvants, it is possible to use as adjuvant (1) aluminum hydroxide, (2) a polymer of acrylic or methacrylic acid, a polymer of maleic anhydride and of alkenyl derivative, or (3) to formulate the immunogenic composition or vaccine in the form of an oil-in-water emulsion, in particular the emulsion SPT described p 147 "Vaccine Design, The Subunit and Adjuvant Approach" edited by M. Powell, M. Newman, Plenum Press 1995, and the emulsion MF59 described p 183 in the same book.

The oil-in-water emulsion may in particular be based on light liquid paraffin oil (European Pharmacopeia type); isoprenoid oil such as squalane, squalene; oil resulting from the oligomerization of alkenes, in particular of isobutene or of decene; esters of acids or alcohols containing a linear alkyl group, more particularly vegetable oils, ethyl oleate, propylene glycol di(caprylate/caprate), glyceryl tri(caprylate/caprate), propylene glycol dioleate; esters of branched fatty alcohols or acids, in particular esters of isostearic acid. The oil is used in combination with emulsifiers to form the emulsion. The emulsifiers are preferably nonionic surfactants, in particular the esters of sorbitan, mannide, glycerol, polyglycerol, propylene glycol and of oleic, isostearic, ricinoleic or hydroxystearic acid, which are optionally ethoxylated, the polyoxypropylene-polyoxyethylene block copolymers, in particular the Pluronic® copolymers, especially L121.

The preferred adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 (incorporated herein by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are cross-linked with an allyl sucrose or with allyl pentaerythritol. Among then, there may be mentioned Carbopol® 974P, 934P and 971P.

Among the copolymers of maleic anhydride and alkenyl derivative, the copolymers EMA® (Monsanto) which are copolymers of maleic anhydride and ethylene, linear or cross-linked, for example cross-linked with divinyl ether, are preferred. Reference may be made to J. Fields et al., incorporated herein by reference.

From the point of view of their structure, the polymers of acrylic or methacrylic acid and the copolymers EMA® are preferably formed of basic units of the following formula:

$$----\underset{\underset{COOH}{|}}{\overset{\overset{R_1}{|}}{C}}-(CH_2)_x-\underset{\underset{COOH}{|}}{\overset{\overset{R_2}{|}}{C}}-(CH_2)_y----$$

in which:
- $R_1$ and $R_2$, which are identical or different, represent H or $CH_3$
- x=0 or 1, preferably x=1
- y=1 or 2, with x+y=2

For the copolymers EMA®, x=0 and y=2. For the carbomers, x=y=1.

The dissolution of these polymers in water leads to an acid solution which will be neutralized, preferably to physiological pH, in order to give the adjuvant solution into which the vaccine itself will be incorporated. The carboxyl groups of the polymer are then partly in $COO^-$ form.

Preferably, a solution of adjuvant according to the invention, especially of carbomer, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCL 9 g/l) all at once in several portions with concomitant or subsequent neutralization (pH 7.3 to 7.4), preferably with NaOH. This solution at physiological pH will be used as it is for mixing with the vaccine, which may be especially stored in freeze-dried, liquid or frozen form.

The polymer concentration in the final vaccine composition will be 0.01% to 2% w/v, more particularly 0.06 to 1% w/v, preferably 0.1 to 0.6% w/v.

Standard texts, such as "REMINGTON'S PHARMACEUTICAL SCIENCE", 17th edition, 1985, incorporated herein by reference, may be consulted to prepare suitable preparations, without undue experimentation.

Compositions in forms for various administration routes are envisioned by the invention. And again, the effective dosage and route of administration are determined by known factors, such as age, sex, weight, condition and nature of the feline, as well as $LD_{50}$ and other screening procedures which are known and do not require undue experimentation. Dosages of each active agent can be as in herein cited documents (or documents referenced or cited in herein cited documents) and/or can range from one or a few to a few hundred or thousand micrograms, e.g., 1 μg to 1 mg, for a subunit immunogenic, immunological or vaccine composition; and, $10^4$ to $10^{10}$ $TCID_{50}$ advantageously $10^6$ to $10^8$ $TCID_{50}$ for an inactivated immunogenic, immunological or vaccine composition.

It is of course possible to also combine inactivated virus and subunits of the same FCV strain in accordance with the invention and/or of different FCV strains in accordance with the invention.

The FCV vaccines according to the invention may be mixed immediately before use with the other feline valency (valencies) which may be in the form of attenuated live, inactivated, subunit, recombinant or polynucleotide vaccines.

However, the dosage of the composition(s), concentration of components therein and timing of administering the composition(s), which elicit a suitable immunological response, can be determined by methods such as by antibody titrations of sera, e.g., by ELISA and/or seroneutralization assay analysis. Such determinations do not require undue experimentation from the knowledge of the skilled artisan, this disclosure and the documents cited herein. And, the time for sequential administrations can be likewise ascertained with methods ascertainable from this disclosure, and the knowledge in the art, without undue experimentation.

In one embodiment, the method of immunization comprises the administration of a combined multivalent, subunit or inactivated FCV vaccine according to the invention to cats. The administration of said vaccine may be carried out in particular by the parenteral route, preferably by the subcutaneous or intramuscular route.

For example, using a vaccine comprising freeze dried components that have been reconstituted with diluent, healthy cats 6 weeks of age and older can be immunized for the prevention of disease due to FCV. A 1 ml dose can be injected intramuscularly or subcutaneously. For primary vaccination, additionally boosters can be given at, for example, 3 to 4 weeks after the initial administration. One of skill in the art can determine appropriate dosing schedules without undue experimentation. For example, cats younger than 12 weeks of age can be revaccinated every 3 to 4 weeks, the last dose given at or over 12 weeks of age. After primary vaccination, boosters can be given annually.

Accordingly, another embodiment of the present invention is a method of immunization felines against FCV comprising at least one administration of an immunogenic or vaccine composition. In another embodiment, at least 2 or 3 or 4 or more administrations of an immunogenic or vaccine composition can be administered.

Persons skilled in the art have the competence necessary to define precisely the number of injections and the doses of each vaccine to be used for each vaccination protocol. For example, in one embodiment, the dose volumes may be in particular between 0.2 and 2 ml, preferably of the order of 1 ml.

Alternatively, needle-free injector may be used for transdermal delivery (intradermal and subcutaneous and possibly intramuscular delivery). The dose volumes may be between 0.1 ml and 1 ml.

Suitable dosages can also be based upon the examples below.

In one embodiment of the invention, the immunogenic or vaccine compositions comprise inactivated FCV. Thus the invention relates to a non-adjuvanted inactivated FCV immunogenic composition or vaccine comprising FCV that has been subjected to an inactivating agent and to a stabilizing aldehyde compound formed of a linear alkyl C1-C5 chain comprising one aldehyde group when the chain is C1 and two terminal aldehyde groups when the chain is C2-C5, and optionally one aldehyde group may be replaced by a cetone or an epoxy group when the chain is the C2-C5 chain, and the immunogenic composition or vaccine is either in freeze-dried form or in a liquid form in a veterinarily acceptable excipient or vehicle.

By definition the inactivating agent is an agent able to block the multiplication of a virus by an irreversible reaction mainly with viral nucleic acids and without substantially affecting the immunogenic property of the virus. Preferred examples of inactivating agents are ethylenimine and the amide derivatives (for example acetylethylenimine), propyleneimine, β-propiolactone. In a preferred embodiment, the inactivating agent is ethylenimine.

In a preferred embodiment, the FCV is inactivated by the action of ethylenimine. The final concentration of ethylenimine may be of from about 0.5 mM to about 20 mM, and preferably of from about 1 mM to about 10 mM. The temperature may be of from about 2° C. to about 40° C., and preferably of from about 5° C. to about 30° C.

The stabilizing aldehyde compounds react on amino groups (e.g. amino groups on lysine, arginine or histidine amino acids) and hydroxyl groups of protein(s) (e.g. hydroxyl groups on tyrosine amino acids) and may form linkages between two proteins and/or within a protein. The stabilizing aldehyde compound is preferably selected from the group consisting of formaldehyde (or methanal), glycidaldehyde (or 2,3-epoxy-1-propanal), glutaraldehyde (or 1,5-dial-pentane), glyoxal (or 1,2-dial-ethane), methylglyoxal (or pyruvaldehyde). In a preferred embodiment the stabilizing aldehyde compound is the formaldehyde.

After completion of inactivation and/or stabilization, it is possible to neutralize the inactivating agent and/or the stabilizing aldehyde compound with techniques known by the man skilled in the art, for example by adding neutralizing compounds comprising thiol groups (e.g. thiosulfate, cysteine).

It is possible with techniques known by the man skilled in the art, for example size exclusion chromatography, ultracentrifugation on a sucrose gradient, ultracentrifugation on a cesium chlorure gradient, selective precipitation for example PEG precipitation (polyethylene glycol), to eliminate the inactivating agent and/or the stabilizing aldehyde compound.

To adjust the stabilization conditions (temperature, concentration of the stabilizing aldehyde compound and duration), a quantification of the FCV virions may be performed. Any appropriated technique allowing to quantify virions may be used, for example an ELISA using a monoclonal or polyclonal antibody specific for the FCV capsid protein. Before ELISA quantification, the virions are separated from the treated viral culture with techniques known by the man skilled in the art, for example size exclusion chromatography, ultracentrifugation on a sucrose gradient, ultracentrifugation on a cesium chlorure gradient, selective precipitation for example PEG precipitation (polyethylene glycol).

With formaldehyde:
The final concentration may be of from about 0.05 g/l to about 0.8 g/l, preferably of from about 0.075 g/l to about 0.6 g/l, and more preferably of from about 0.1 g/l to about 0.5 g/l.
The temperature may be of from about 2° C. to about 37° C., preferably of from about 2° C. to about 22° C., and more preferably of from about 4° C. to about 7° C.

In one embodiment of the invention, the immunogenic composition or vaccine comprises freeze-dried stabilized and inactivated FCV and a freeze-drying excipient, for example, amino acids e.g. glutamic acids, carbohydrates e.g. lactose, and mixtures thereof e.g. SPGA (sucrose/phosphate/glutamate/albumin; EP-A-0.496.135). In another embodiment, the immunogenic composition or vaccine is liquid and comprises the FCV in a physiological solution or buffer.

Another embodiment of the invention is a process to produce inactivated and stabilized FCV, comprising reacting FCV with an inactivating agent and a stabilizing aldehyde compound formed of a linear alkyl C1-C5 chain comprising one aldehyde group when the chain is C1 and two terminal aldehyde groups when the chain is C2-C5, and optionally one aldehyde group may be replaced by a cetone or an epoxy group when the chain is the C2-C5 chain. Preferred embodiments for the inactivating agent and the stabilizing aldehyde compound and their conditions of use have been described above.

The process of the invention comprises the culture of FCV, the treatment with the inactivating agent and the stabilizing aldehyde compound. The addition of the stabilizing aldehyde compound can be done before, during or after the inactivation step. Neutralisation of the inactivating agent and/or the stabilizing aldehyde compound may be performed as described above.

The stabilized inactivated FCV virions may be concentrated by conventional concentration techniques, for example by ultrafiltration and then optionally purified by conventional purification means, for example size exclusion chromatography, ultracentrifugation on a sucrose gradient, ultracentrifugation on a cesium chlorure gradient, or selective precipitation for example in the presence of polyethylene glycol (PEG). Inactivated and stabilized FCV may be stored at about 5° C.

It is to be understood as a further embodiment of the invention that any of the immunogenic or vaccine compositions described herein can comprise inactivated FCV, which FCV may be inactivated using any of the methods herein described.

In a further embodiment of the invention, there is provided a multivalent vaccination kit or box comprising, packaged separately, an FCV valency according to the invention in a veterinarily acceptable vehicle or excipient, and preferably with an adjuvant, and at least one valency of another feline pathogen. The FCV valency can serve as solvent for another feline valency, in particular attenuated, recombinant or polynucleotide valency provided in freeze-dried form.

EXAMPLES

Example 1

Viral Isolates and Hybridomas

The feline caliciviruses (FCV) were obtained by pharyngeal swabs taken on cats exhibiting signs of infection with feline caliciviruses. These FCVs have different geographical origins.

The FCV 431, 337, J5, 388b, 220 and 393 strains were isolated in Great Britain and provided by Professor O. Jarrett of the University of Glasgow, UK.

The FCV A2, G1, G3, F3031, F1, H3-2 and H1-4 strains were isolated in France by the Applicant.

The FCV RMI1, RMI2, RMI3, RMI5, RMI6, RMI7 and FMI9 strains were isolated in the USA by the Applicant.

The pharyngeal samples were collected in 2 ml of Dulbecco's modified Eagle's minimum medium (DMEM, Gibco BRL), supplemented with 5% fetal calf serum (Bayer Diagnostic), with antibiotics, more particularly with 50 mg/l of gentamycin. Each isolate is frozen at −70° C. while waiting to be tested. The monoclonal antibody 44, obtained from the hybridoma identified 431 2 0 17 E9 T, is specific for the FCV 431 strain.

Example 2

Amplification of the Viral Isolates

Cells of the cat kidney line (Crandell-Reese Feline Kidney or CRFK No. ATCC CCL-94, Crandell et al. In Vitro 1973. 9. 176-185) are cultured in a 96-well plate or in a 25-$cm^2$ Falcon (Falcon) with DMEM medium supplemented with 5% fetal calf serum, containing about 100,000 cells per ml. The cells are cultured at 37° C. in an atmosphere containing 5% $CO_2$. After 3 days, the cell layer arrives at confluence. The culture medium is then replaced with serum-free DMEM medium supplemented with 50 mg/l of gentamycin and the thawed aliquot of the FCV viral isolates (Example 1) are added at the rate of a volume of 100 µl of four-fold serial dilutions per well for the limiting dilution cloning of the FCV viruses or of 1 ml per Falcon.

When the cytopathic effect (ECP) is complete (24-48 hours after the start of the culture), the viral suspensions are harvested and frozen at −70° C. 3 to 4 successive passages are generally necessary for the production of a viral batch. The viral batch is stored at −70° C.

Example 3

Production of Serum

For each FCV virus, an antiserum was produced by inoculating kittens by the oronasal route with $10^{6.0}$ $CCID_{50}$ of the relevant FCV virus. The specific pathogen-free (SPF) kittens were 10 to 14 weeks old. The serum of each animal was collected one month after the infection. The sera were heat-inactivated (30 minutes at 56° C.), distributed, aliquoted and stored at −20° C.

Example 4

Cross-Serum Neutralization in vitro

Cross-serum neutralization tests were carried out between 18 field isolates obtained by pharyngeal swabs performed on cats exhibiting signs of feline calicivirosis. 7 of them have as geographical origin France, they are the isolates identified A2, F3031, G1, G3, F1, H3-2 and H1-4. 4 have as geographical origin Great Britain, they are the isolates identified J5, 337, 388b and 431. Finally, 7 have as geographical origin the USA, they are the isolates identified RMI1, RMI2, RMI3, RMI5, RMI6, RMI7 and RMI9.

The serum obtained for each isolate (Example 3) was tested for its ability to neutralize the 18 isolates. The sera were three-fold serially diluted with DMEM medium in 96-well cell culture plates. 0.05 ml of culture medium containing approximately 100 $CCID_{50}$ of the selected viral strain was added to 0.05 ml of the dilute serum produced as in Example 2. This mixture was incubated for 2 hours at 37° C. in an incubator under an atmosphere containing 5% $CO_2$.

0.15 ml of a suspension of CRFK cells containing about 100,000 cells per ml was then added to each mixture. The cytopathic effect was observed by phase contrast microscopy after 4 days of culture at 37° C. in an atmosphere containing 5% $CO_2$. The neutralizing titers of each serum were calculated according to the Karber method. The titers are given in the form of the highest dilution inhibiting the cytopathic effect for 50% of the wells. The titers are expressed in $log_{10}$. The minimum titer thus found was 0.7 $log_{10}$ $VN_{50}$. Each serum was titrated at least twice, preferably three times.

FIG. 1 gives all the neutralizing titers obtained during cross-serum neutralizations carried out between these 18 FCV strains and these 18 sera.

Example 5

Indirect Immunofluorescence (IIF) Tests

The IIF tests are carried out on 96-well plates containing the CRFK cells cultured in monolayers infected with the FCV viruses to be tested.

200 μl per well of a suspension of CRFK cells containing 90,000 cells/ml in F15 medium (Gibco BRL, Cat #045-1075) containing 5% fetal calf serum are cultured in a 96-well plate. At confluence, 320 CCID50 of FCV are inoculated in 100 μl of F15 medium. When the first CPE foci appear, the cells are then rinsed with cold PBS with no calcium or magnesium (PBS, Sigma), and then fixed at −20° C. for 30 minutes with cold acetone containing 5% v/v of water. After drying, the infected and fixed cells are brought into contact for 30 minutes at 37° C. with 100 μl per well of ascitic fluid corresponding to the anti-FCV 431 monoclonal antibody 44 (hybridoma 431 2 0 17 E9 T, diluted 1/5000 approximately in 50 mM TRIS-HCl buffer, pH 7.6.

After two rinses in PBS, the attachment of the antibodies is visualized by incubation under the same conditions of a goat anti-mouse IgG antibody conjugated with fluorescein isothianate (Biosys, FITC conjugated at 2 mg/ml) and diluted 1/150 in 50 mM TRIS-HCl buffer, pH 7.6. The reading is made under an optical microscope under UV light.

This monoclonal antibody was tested with respect to each of the isolates of the panel. It is attached exclusively to the CRFK cells infected with FCV 431.

This test may be used to determine the equivalents of the FCV 431 strain. These equivalents are those to which the monoclonal antibody 44 attaches.

It is noted that monoclonal 44 is a neutralizing and conformational antibody and that neutralization is correlated with protection. FIG. 2 shows IFA profiles of isolates by using anti-p66 (FCV 431) monoclonal antibodies; monoclonal antibody 44 is specific to FCV 431.

Example 6

Synergy 32 nonvaccinated SPF kittens about 9 weeks old are divided by randomization into 4 groups (identified from A to D) of 8 kittens each, each group is housed in an isolated box.

After thawing the viral suspensions (Example 2) and diluting in PBS so as to obtain the desired titer, the cats are vaccinated by subcutaneous injection of 1 ml of FCV G1 inoculum at $10^{3.3}$ $CCID_{50}$/ml for group B, of 1 ml of FCV 431 inoculum at $10^{3.5}$ $CCID_{50}$/ml for group C, of 0.5 ml of FCV G1 inoculum at $10^{3.3}$ $CCID_{50}$/ml and 0.5 ml of FCV 431 inoculum at $10^{3.5}$ $CCID_{50}$/ml (at a different injection site) for group D. Group A serves as control group.

Half of each group A to D is randomly distributed into two groups 1 and 2 and housed in separate boxes. The animals are challenged on the $31^{st}$ day after vaccination (d31).

The animals in group 1 are challenged by administration of 1 ml of challenge viral strain FCV 220 having a titer of $10^{7.2}$ $CCID_{50}$/ml by the oronasal route (0.5 ml by the oral route and 0.25 ml into each nostril).

The animals in group 2 are challenged by administration of 1 ml of challenge viral strain FCV 393 having a titer of $10^{6.8}$ $CCID_{50}$/ml by the oronasal route (0.5 ml by the oral route and 0.25 ml into each nostril).

The virulent strains FCV 220 and 393 were chosen because they are distant in cross-serum neutralization from the viral strains FCV G1 and 431.

Any cross-contamination between the two boxes is carefully avoided. Clinical monitoring of the animals in both groups is done by taking the rectal temperature and clinical examinations of the animals (general state, presence of ulcers of the tongue and of the palate, presence of gingivitis, presence of rhinitis, presence of conjunctivitis, presence of lameness, death of the animal).

The total clinical score for each animal was calculated by adding the scores obtained for each group of clinical signs according to the following scale:

rectal temperature:
    0—less than 39° C.
    1—greater than or equal to 39° C. and less than 39.5° C.
    2—greater than or equal to 39.5° C. and less than 40° C.
    3—greater than or equal to 40° C.
general state:
    0—normal behavior
    1—exhaustion
ulcers of the tongue and of the palate (some of the diameters of all the ulcers, if there are several):
    0—absence of ulcer
    1—diameter of 1 to 5 mm
    2—diameter of 6 to 10 mm
    3—diameter greater than 10 mm
gingivitis:
    0—absence of gingivitis
    1—gingivitis
rhinitis:
    0—absence of rhinitis
    1—rhinitis with serous nasal discharge
    2—rhinitis with mucous to mucopurulent nasal discharge
conjunctivitis:
    0—absence of conjunctivitis
    1—conjunctivitis with serous discharge
    2—conjunctivitis with mucopurulent discharge
lameness:
    0—absence of lameness
    1—lameness
death:
    0—survival
    5—death.

The mean clinical scores obtained are the following:

| Group/challenge | FCV 220 | FCV 393 |
| --- | --- | --- |
| Control (group A) | 31 | 30 |
| FCV G1 (group B) | 5 | 23 |
| FCV 431 (group C) | 6 | 18 |
| FCV G1 + FCV 431 (group D) | 2 | 9 |

The results thus obtained show synergy between the FCV G1 and FCV 431 strains by a significant difference between the mean value obtained for the best strains and that obtained for the combination of the two strains (Kruskal-Wallis test).

Example 7

Production of Inactivated Vaccine

The CRFK cells are cultured at 37° C. in 2-liter roller flasks (850 cm$^2$) in modified Eagle's medium (MEM, Gibco BRL) supplemented with 2.5% of lactalbumin hydrolysate (Gibco BRL) and 5% fetal calf serum (Gibco BRL). 300 ml of a cellular suspension in MEM medium containing about 100,000 cells/ml are added per roller flask. After 3 days, the cell layer becomes confluent. The cell culture medium is then replaced with serum-free MEM and the FCV virus added at a multiplicity of infection (moi) of 0.5 CCID$_{50}$/cell. The viral culture is maintained at 37° C. for 24 to 48 hours until a cytopathic effect is obtained for the whole cellular lawn. The viral suspension is harvested and then clarified on a bag filter having a porosity of 1.5 μm. The FCV virus titer at harvest is 8.5+/−0.3 log 10 CCID$_{50}$/ml.

The virus is inactivated with ethylenimine at the concentration of about 8 mM at 22° C. for 18 hours.

The ethylenimine is prepared immediately before use by dissolving 28 g of sodium hydroxide pellets in 200 ml of distilled water and adding 68.1 g of bromoethylamine (BEA) corresponding to a 1.2 M solution approximately (H. Bahnemann, Arch. Virol., 1975, 47, 47-56). The inactivated viral suspension is concentrated 100-fold on an Ultrasette-type ultrafiltration cartridge with a cut-off of 100 kDa (Filtron) and then frozen at −70° C.

The inactivated viral suspension after thawing is diluted 1/33 in PBS buffer (NaCl 8 g/l; KCl 0.2 g/l; KH$_2$PO$_4$ 0.2 g/l; Na$_2$HPO$_4$, 2H$_2$O 1.44 g/l). The vaccine is prepared in the same manner: 167 ml of aqueous phase consisting of the dilution of the inactivated virus are emulsified in 83 ml of an oily phase containing 7% w/v of anhydromannitol oleate, 8% w/v of ethoxylated oleic acid containing 11 molecules of ethylene oxide (EO) on average and 85% v/v of light liquid paraffin oil (European Pharmacopeia type) with the aid of a Silverson turbine emulsifier at 32° C. for 2 minutes. The vaccine is then stored at 5° C.

An alternative method for preparing the vaccine consists in forming into an emulsion by three passes through a model Y110 high-pressure homogenizer (Microfluidics Corp.) at a pressure of 600 bar and a temperature of between 30 and 40° C. the mixture 5% w/v squalane, 2.5% w/v Pluronic® L121, 0.2% w/v Tween 80, 92.3% v/v of inactivated viral suspension diluted 1/46 in PBS buffer after thawing. The vaccine is then stored at 5° C.

Another alternative method consists in preparing a solution containing 0.4% w/v of Carbopol® 974P in physiological saline (NaCl 9 g/l). The pH is adjusted to 7.3-7.4 with sodium hydroxide. This solution of Carbopol® is then mixed in equal parts with the suspension of inactivated FCV virus diluted 1/25 after thawing. The vaccine is then stored at 5° C.

The aqueous phase of the emulsions or the aqueous phase mixed with Carbopol® consists of a dilution in PBS of the concentrated inactivated viral suspension corresponding either to the FCV 431 strain or to the FCV G1 strain or a mixture in equal parts of the FCV 431 and G1 strains.

Example 8

Immunogenicity of Inactivated FCV 431

19 nonvaccinated SPF kittens about 9 weeks old are divided by randomization into 2 groups (identified from A and B), the first with 12 kittens and the second with 7 kittens, each group is housed in an isolated box.

The vaccine is prepared with the adjuvant composed of anhydromannitol oleate, ethoxylated oleic acid and light liquid paraffin oil as described in Example 7.

The cats are vaccinated twice (D0 and D28) by subcutaneous injection of 1 ml of FCV 431 inoculum at 10$^7$ CCID$_{50}$/ml for group A. Group B serves as control group.

The animals are challenged on the 42$^{nd}$ day after the first vaccination (D42) by administration of 1 ml of challenge viral strain FCV 431 having a titer of 10$^6$ CCID$_{50}$/ml by the oro-nasal route (0.5 ml by the oral route and 0.25 ml into each nostril).

The level of anti-FCV 431 neutralizing antibodies and the clinical score were monitored. The total clinical score for each animal was calculated by adding the scores obtained for each group of clinical signs according to the scale given in Example 6.

The results obtained are the following:

Anti-FCV 431 neutralizing antibody titers expressed as $\log_{10} VN_{50}/ml$:

| Group | Antibody on D0 | Antibody on D28 | Antibody on D42 |
|---|---|---|---|
| FCV 431 vaccine (group A) | 0.24 | 1.61 | 2.87 |
| Controls (group B) | 0.24 | 0.24 | 0.24 |

Mean clinical scores over the period D42 to D56:

| Group | Clinical score |
|---|---|
| FCV 431 vaccine (group A) | 0.7 |
| Controls (group B) | 33.7 |

These results show an excellent clinical protection against the homologous challenge and good seroconversion.

Example 9

Preparation of Inactivated and Stabilized FCV 100869 Viruses

CRFK cells (Crandell-Reese Feline Kidney cells, accessible from the American Type Culture Collection under the number CCL-94) were cultured in biogenerator at 37° C., pH 7.2, 30% of oxygen and 50 rpm (rotation per minute). The culture medium was constituted with modified Eagle's medium (MEM, Gibco BRL) supplemented with 5% fetal calf serum and added with 1.5 g/l of Cytodex 1 microcarriers. The cells were introduced into the culture at a final concentration of 0.2 $10^6$ cells/ml.

After 4 days, the agitation was stopped and the microcarriers were separated by decanting. The cell culture medium was replaced with serum-free MEM and strain 100869 FCV virus added at a multiplicity of infection (moi) of 0.5 $CCID_{50}$/cell. The viral culture was maintained at 37° C., pH 7.2, 30% of oxygen and 50 rpm for 18 hours until a cytopathic effect was obtained.

The suspension was cooled to 10° C. and agitated strongly prior to the agitation being stopped and the microcarriers were then separated by decanting and were eliminated.

The viral suspension was harvested and clarified on a filter having a porosity of 1.5 μm.

The viral suspension was inactivated with ethylenimine at a concentration of 8 mM at 22° C. for 18 hours. The ethylenimine was prepared by dissolving 36 g of sodium hydroxide pellets in 257.5 ml of distilled water and adding 87.5 g of bromoethylamine (BEA) corresponding approximately to a 1.2 M solution of ethylenimine.

At the end of the 18 hour inactivation period, the inactivated viral suspension was stabilized by the addition of formaldehyde at a final concentration of 0.5 g/l and agitated at 10° C. for 24 hours.

The inactivated and stabilized viral suspension was concentrated by ultrafiltration about twelve times on a 150 kDa cut-off membrane.

The inactivated, stabilized and concentrated viral suspension was purified by gel-filtration chromatography (BPG 100/950 column packed with 6FF Sepharose) with a charge buffer and elution buffer comprising phosphate buffer saline (PBS) without calcium and without magnesium, pH 7.4.

The viral fraction was concentrated by ultrafiltration approximately 100 times on 100 kDa cut-off membrane.

Example 10

Cross-Serum Neutralization in vitro

Cross-serum neutralization tests were performed using the same techniques as described above in Example 4. The cross-serum neutralization tests were carried out between a total of 51 strains of feline calicivirosis. These strains included:

A2, F1, G1, H3-2, G3, F3031, H1-4, and F3, all of which originated in France;

388b, 431, 419, 337, J1, J5, 220, and 393, all of which originated in the United Kingdom;

RMI1, RMI2, RMI3, RMI4, RMI5, RMI6, RMI7, RMI8, RMI9, 98A-13445, 98A-4417, 98A-49529, 98A-4568, 968384-97, 31383-97, 98A-46260, 941421-96, 98A-8107, 98A-49526, 93182-98, 98A-10305, 98A-49052, all of which originated in the United States; and 94580, 33585-1, 89391, 88287, 100869-1, all of which originated in the United States and are considered hypervirulent.

Serum was obtained from cats after immunization with live strains of each isolate. Serum was also obtained after vaccination with commercially available vaccines, specifically those which used strains 255 and F9.

The serum was tested for its ability to neutralize the 51 isolates. The sera were three-fold serially diluted with DMEM medium in 96-well cell culture plates. 0.05 ml of culture medium containing approximately 100 $CCID_{50}$ of the selected viral strain was added to 0.05 ml of the dilute serum. This mixture was incubated for 2 hours at 37° C. in an incubator under an atmosphere containing 5% $CO_2$.

0.15 ml of a suspension of CRFK cells containing about 100,000 cells per ml was then added to each mixture. The cytopathic effect was observed by phase contrast microscopy after 4 days of culture at 37° C. in an atmosphere containing 5% $CO_2$. The neutralizing titers of each serum were calculated according to the Karber method. The titers are given in the form of the highest dilution inhibiting the cytopathic effect for 50% of the wells. The titers are expressed in $\log_{10}$. The minimum titer thus found was 0.7 $\log_{10}$ $VN_{50}$. Each serum was titrated at least twice, preferably three times.

Results of the neutralizing titers are shown in FIG. 3. Strains G1 and 431 showed broad cross-neutralization that included successful neutralization of 93% and 98%, respectfully, of all sera tested, and were successful against at least some sera from all geographic locations, including the hypervirulent U.S. strains. In addition, hypervirulent strains 94580, 89391, 88287 and 100869 also showed broad cross-neutralization, with successful neutralization of 100%, 86%, 100%, and 93%, of all strains, respectively.

A chart and graph comparing the cross-serum neutralization activity for each strain as a percentage of total strains, European strains and U.S. strains is found in FIG. 4. The broad cross-neutralization shown in FIGS. 3 and 4 by strains including G1, 431, 94580, 89391, 88287 and 100869 indicate that these strains can be highly effective when used in vaccine preparations against FCV infection.

Example 11

Efficacy of the M725 Vaccine Against FCV100869

Five 8-week old SPF kittens were vaccinated on D0 and D28 with RMB725. RB725 was obtained by reconstituting freeze dried pellets with comprising a vaccine against feline rhinotracheitis (attenuated FHV F2 strain), calicivirosis (inactivated FCV G1/431 antigens), chlamydiosis (attenuated 905 strain of chlamydophila felis), infectious panleucopenia (attenuated PLI IV strain) with a vaccine against feline leukaemia (canarypox–FeLV=vCP97) as a diluent. The vaccine was constituted such that each dose contained 2.67 $\log_{10}$ ELISA units of FCV431/G1 antigen.

On D56, the vaccinated kittens and 5 controls were challenged with FCV100869 via the oronasal route. FCV 100869-1 is an hypervirulent strain that is antigenically distinct from the vaccinal strains. The challenge strain was diluted in physiological saline buffer (pH 7.15) so as to obtain a suspension titrating between 6.0 to 6.5 $\log_{10}$ CCID50/mL.

Following challenge, the kittens were monitored for clinical signs, FCV excretion and ELISA antibodies. Clinical scores were assessed in accordance with European Pharmacopoeia Monograph No. 1101 to define the intensity of the symptoms, as follows:

|  |  | Score |
|---|---|---|
| Rectal temperature | 37° C. < T° < 39.5° C. | 0 |
|  | T° ≧ 39.5° C. | 1 |
|  | T° ≦ 37° C. | 2 |
| General body condition | Good | 0 |
|  | Depression | 2 |
|  | Death (or euthanasia for ethical reason) | 10 |
| Oronasal ulceration | Absence | 0 |
|  | Small and few in number | 1 |
|  | Large and numerous | 3 |
| Nasal discharge | Absence | 0 |
|  | Slight | 1 |
|  | Copious | 2 |
| Ocular discharge | Absence | 0 |
|  | Presence | 1 |
| Oedema of the face or limbs | Absence | 0 |
|  | Presence | 1 |
| Cutaneous ulceration and/or necrosis (face, ears or foot pad) | Absence | 0 |
|  | Presence | 1 |
| Weight loss between the concerned day and the previous day of weighing | Absence | 0 |
|  | Presence | 2 |

Pharyngeal swabs were collected 2, 4, 6, 8, 10 and 14 days after challenge (i.e. at D56, D58, D60, D62, D64, D66 and D70). The swabs were stored at −70° C. in F15 medium enriched with antibiotics (3 mL of medium/swab) until viral isolation. Blood samples were obtained on dry tubes the day of challenge (D56) and 14 days later (D70). Sera were stored at −20° C. until titration of FCV antibodies.

All the control cats developed clinical signs after challenge. Oronasal ulcers (large and numerous for 3 out of 5 controls and small and few for 2 out of 5 controls) and nasal discharge lasting 3 (1 out of 5 controls) or 6 to 8 days (4 out of 5 controls) were observed in all of the control animals. Ocular discharge was recorded in one cat. In addition, one control cat showed depression.

In contrast, the vaccinated cats presented with less severe clinical signs: Specifically, oronasal ulcers of small size developed in 2 out of 5 vaccinated cats and no ulcers of any size developed in the remaining vaccinated cats. Also, vaccinated cats developed slight nasal discharge lasting 1-2 days (3 out of 5 vaccinates) or 4-6 days (2 out of 5 vaccinates). None of the vaccinated cats developed ocular discharge.

Figure 5:
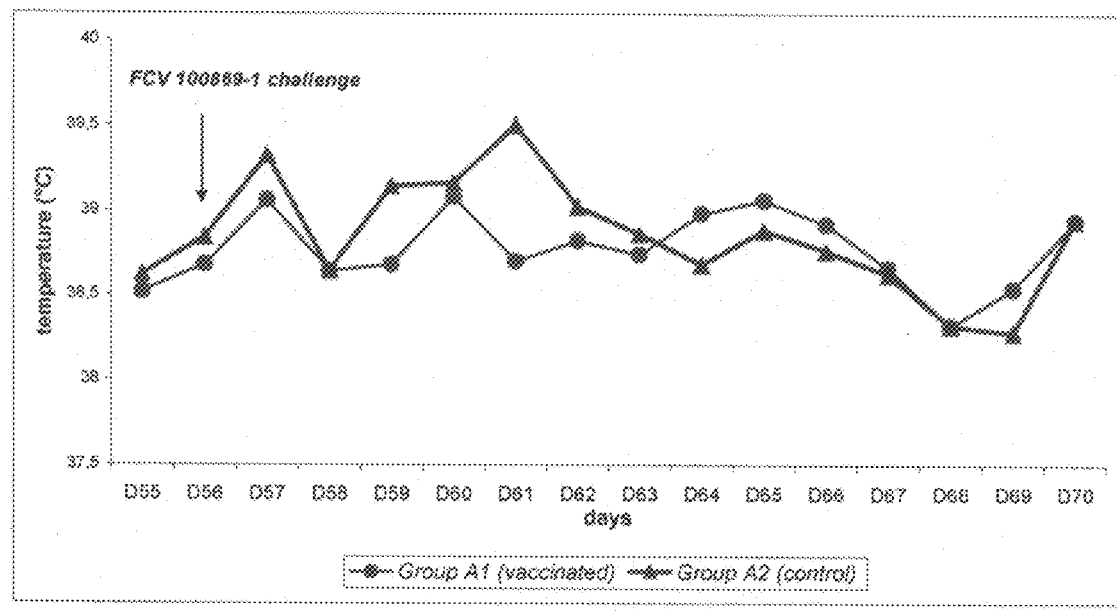
FIG. 5 is a graph depicting the changes in temperature of felines after challenge with FCV 100869.

Hyperthermia was recorded in 3 out of 5 controls on one to five separate occasions on days 1 to 6 after challenge. In contrast, no vaccinated cat presented with hyperthermia. Hyperthermia peaked at D61 for the control animals, as shown in FIG. 5.

Figure 6:
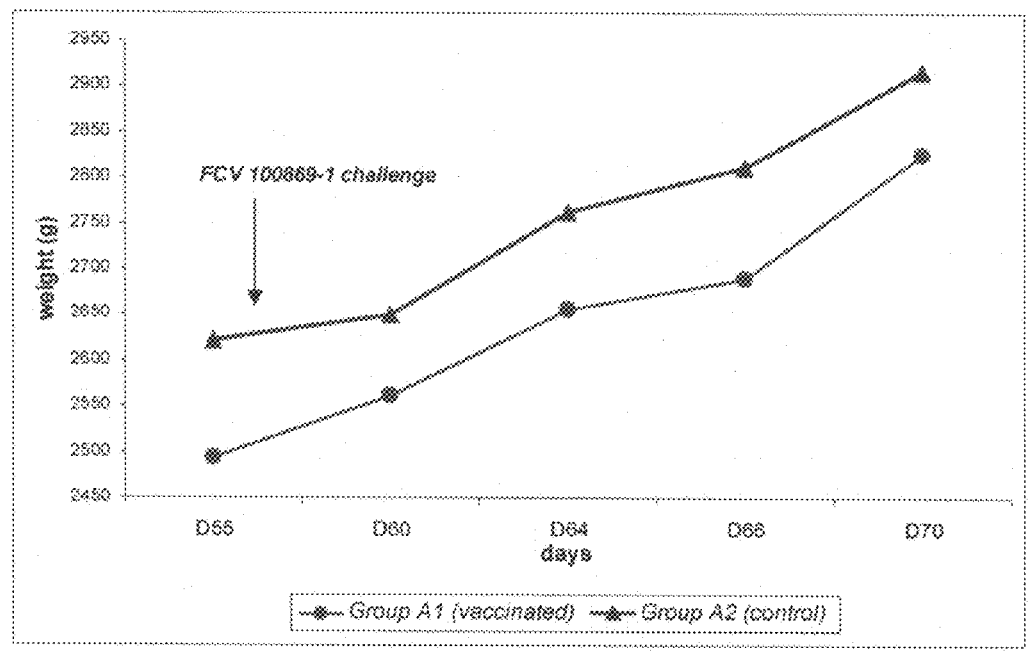
FIG. 6 is a graph depicting the changes in weight of felines after challenge with FCV 100869.

Kittens were weighed at one day before challenge, and at 4, 8, 10, 12 and 14 days after challenge (i.e. at D55, D60, D64, D66 and D70). Growth was poorly affected by the challenge, with punctual weight loss being recorded in 2 out of 5 controls versus 1 out of 5 vaccinates. On average, growth was slower in the control animals than in the vaccinates. The mean weight of vaccinated cats at D70 was underestimated and appeared lower than controls because of the exclusion of one vaccinated cat whose weight had not been recorded. Nevertheless the relative daily weight gain was higher for vaccinates than for controls (8.8 versus 7.2), as is depicted in FIG. 6.

Figure 7:
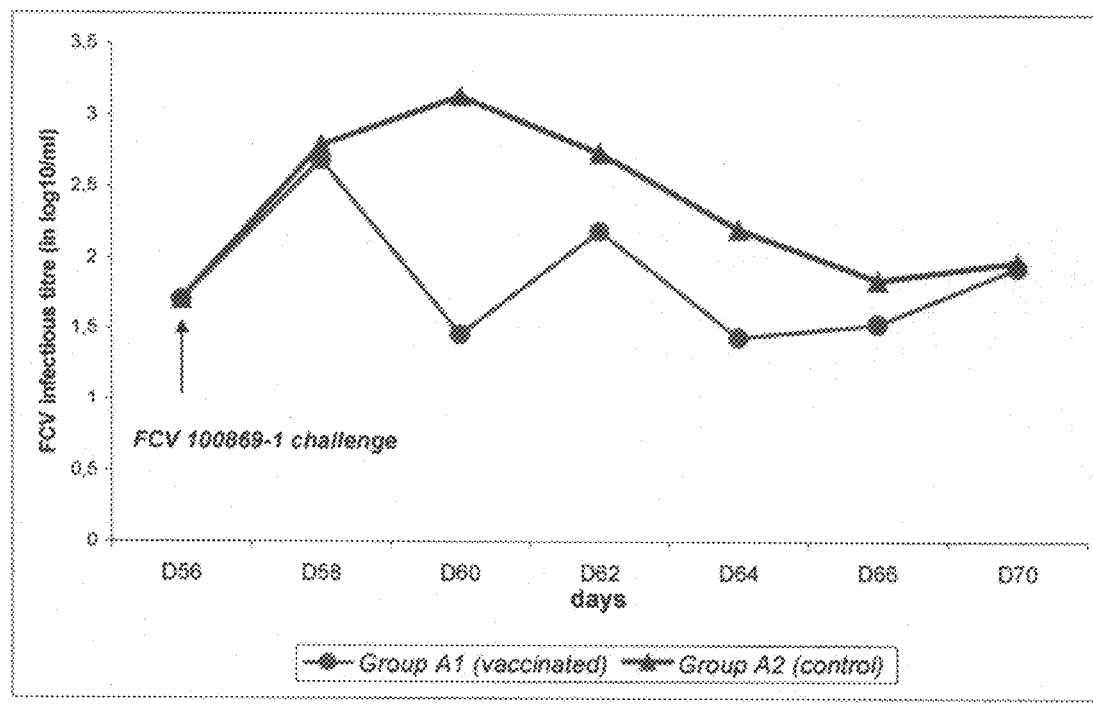
FIG. 7 is a graph depicting the infections titre of felines after challenge with FCV 100869.

All control cats presented with FCV excretion reaching high titres at D60 and decreasing from D62 until the end of the observation period. FCV excretion peaked at D58 in vaccinates then decreased and was under the limit of detection from D64 on with the exception of one cat at D70. Viral shedding was observed in all vaccinates but was very low for 2 vaccinates. In average, viral excretion was higher and lasted longer in controls than in vaccinates as shown in FIG. 7 (ANOVA on the area under the curve; p=0.007).

Figure 8:
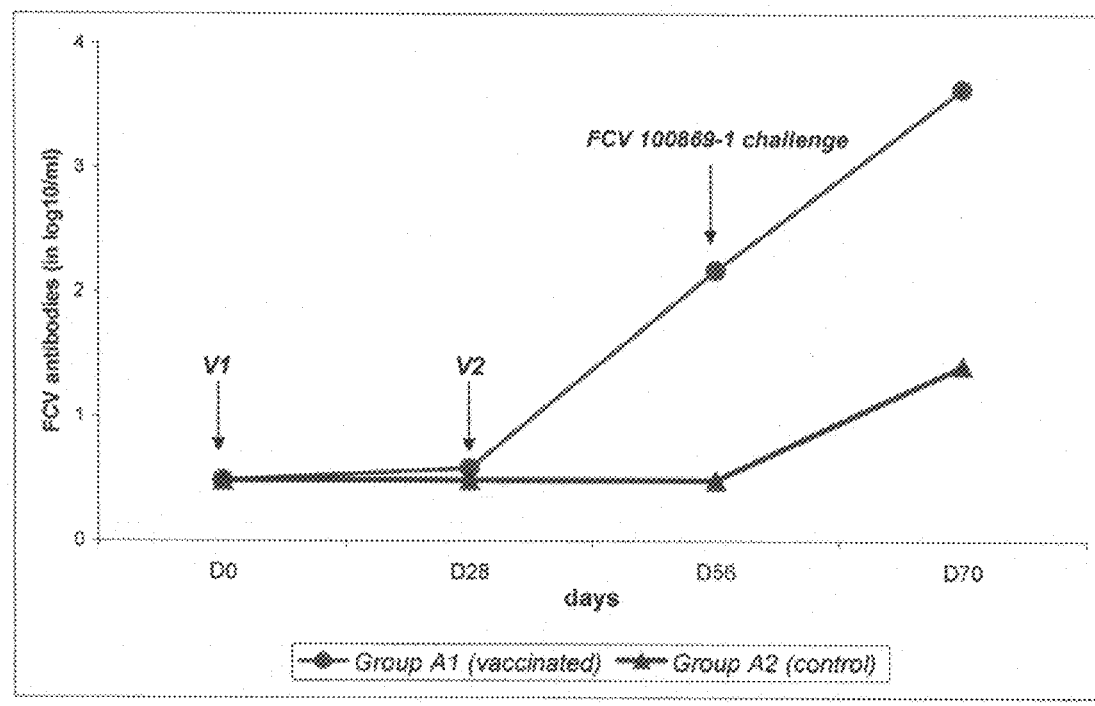
FIG. 8 is a graph depicting the changes in FCV antibodies in felines before and after challenge with FCV 100869.

The cats were evaluated for development of FCV antibodies, and it was determined that all vaccinated cats developed FCV antibodies after the second injection, whereas the controls remained seronegative. The challenge induced a booster effect in the vaccinates and the production of FCV antibodies in control cats. The mean FCV antibody titres per group after challenge is shown in FIG. 8.

Figure 9:
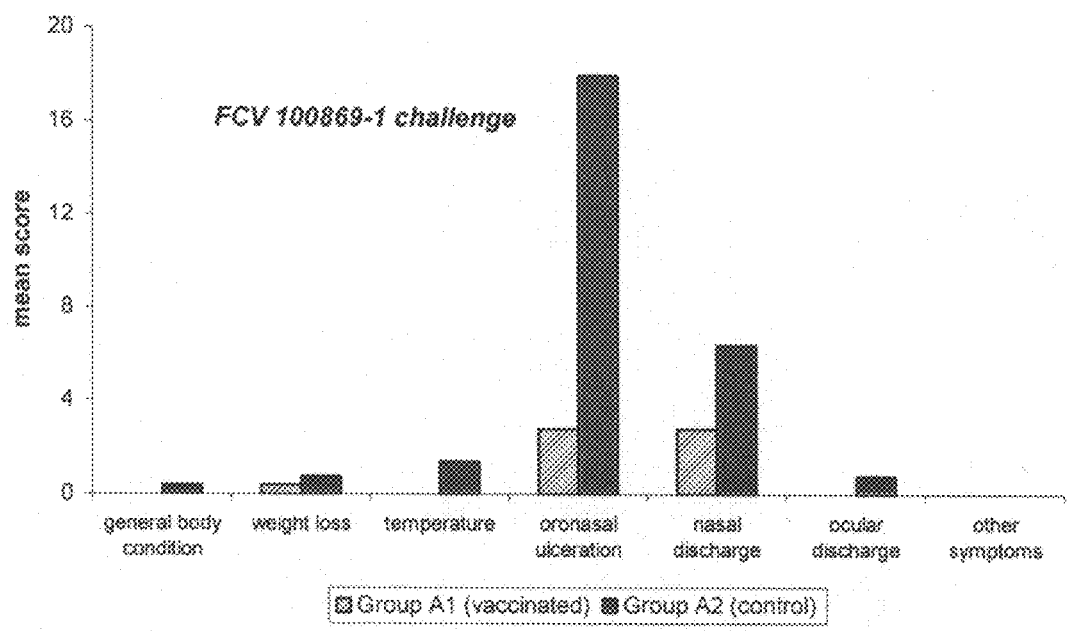
FIG. 9 is a graph summarizing the prevalence of symptoms following challenge with FCV 100869.

Overall, the mean global score of the control group (27.8) was higher (4.6×) than the score for the vaccinated group (6) (ANOVA; p=0.01). This difference was mainly linked to the oronasal ulcers which were much more severe in controls than in vaccinates. In addition, scores of all the other clinical parameters (general body condition, loss of weight, hyperthermia, nasal and ocular discharges) were higher in controls than in vaccinates, as shown in FIG. 9. It can therefore be concluded that the RMB725 vaccine was successful in protecting vaccinated cats from challenge with FCV 100869-1.

Example 12

Efficacy of the M725 Vaccine Against FCV100869

Example 11 was repeated using the same vaccine but having a lower FCV antigen content (2.05 log 10 ELISA units/dose versus 2.67 log 10 ELISA units of FCV431/G1 antigen). In addition, a reduced number of animals was used in each group. As a result, no statistical analysis was performed because of the low number of animals included in this study.

Figure 10:
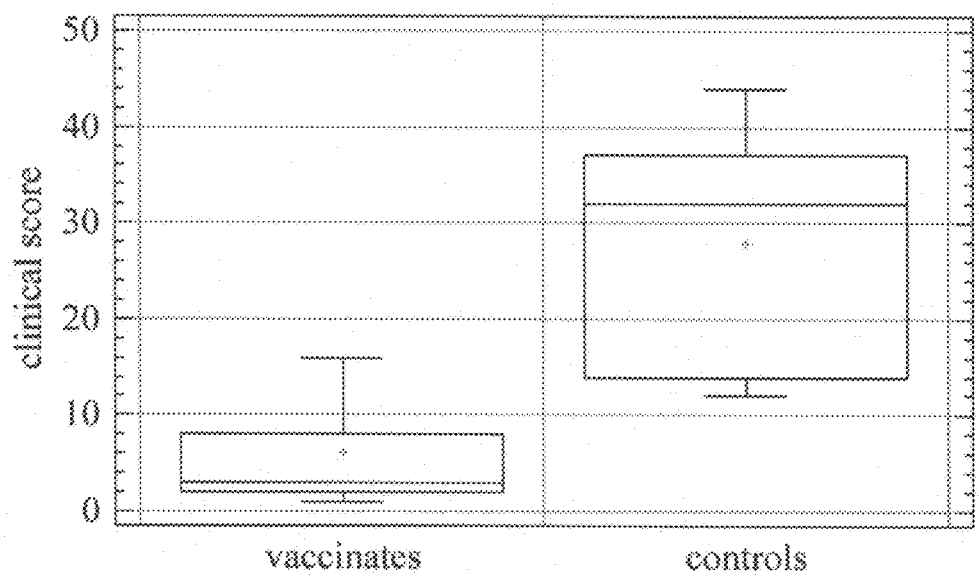
FIG. 10 is a graph depicting the total clinical score of vaccinated and control animals following challenge with FCV 100869.

As shown in FIGS. 10 and 11, the administration of the vaccine reduced systemic and local clinical signs in spite of the severity of the challenge and the low antigen content in the vaccine. Although one of the two controls died of hypervirulent FCV infection, the both vaccinated cats survived the challenge.

In this experiment, the severity of the challenge was related to inoculum titre. A very high titre was used to induce hypervirulent infection. This is consistent with reports from the field suggesting that adults might be more sensitive to FCV hypervirulent strains than kittens (a similar phenomenon is reported with RHDV in rabbits). Consequently, it has now been shown that even in the presence of a challenge with a high inoculum titre, the vaccination was sufficient to significantly reduce the symptoms developed by the vaccinated cats in comparison to control cats.

Example 13

Immunogenicity of Inactivated and Stabilized FCV 100869

18 SPF (specific pathogen free) kittens, 8 weeks old, will be randomized into 3 groups of 6 animals.

Inactivated and stabilized FCV 100869 viruses (obtained as described in 03.0699.P) are diluted in physiological water, pH 7.1. The vaccine A contains a quantity of viruses equivalent to 5 ml of crude culture of FCV before inactivation per dose of 1 ml. The vaccine B contains a quantity of viruses equivalent to 5 ml of crude culture of FCV before inactivation per dose of 0.4 ml.

The kittens of group A receives one dose of vaccine A at each of D0 and D 28. The doses are administered subcutaneously with a syringe and a needle. The kittens of group B receives one dose of vaccine B at each of D0 and D 28. The doses are administered by a needle free injector, Vitajet®. The kittens of group C remain unvaccinated as control animals.

On day 56, all the kittens (vaccinated and unvaccinated) are challenged by oronasal route with a hypervirulent and heterologous FCV strain (FCV 94580 strain) (0.25 ml per nostril and 0.5 ml orally, $10^{6.0}CCID_{50}$/ml).

Anti-FCV neutralizing antibodies, animal weights, rectal temperatures, general conditions, general and local symptoms and viral excretions are observed during the two weeks post-challenge.

The scoring used for the calculation of the global score is as follow:

| Parameters | Observation | Score |
|---|---|---|
| Rectal temperature | T° ≧ 39.5° C. | 1 |
| | T° ≦ 37° C. | 2 |
| General body condition | Depression | 2 |
| | Death | 10 |
| Oronasal ulceration | Small and few in number | 1 |
| | Large and numerous | 3 |
| Nasal discharge | Slight | 1 |
| | Copious | 2 |
| Ocular discharge | Present | 1 |
| Weight | Weight loss | 2 |
| Visage or member edema | Present | 1 |
| Cutaneous necrosis or ulceration | Present | 1 |

It should be clearly understood that the invention defined by the appended claims is not limited to the specific embodiments indicated in the description above, but encompasses the variants which do not depart from the scope or the spirit of the present invention.

REFERENCES

Bahnemann, H. Binary ethylenimine as an inactivant for foot-and-mouth disease virus and its application for vaccine production. *Arch. Virol.* 1975; 47(1):47-56.

Baker, R. J. Oncology: Feline Fibrosarcomas in Vaccination Sites. *Feline Practice.* 1998; 26(5):18-20.

Baulch-Brown, C. et al. Feline calicivirus: a need for vaccine modification? *Aust. Vet. J.* 1997. 75(3):209-213.

Bittle et al. *Am. J. Vet. Res.* 1960. 21:547-550.

Clarke and Lambden (1997) J. Gen. Virol. 8: 291-301.

Coutts et al. Isolation of feline respiratory viruses from clinically healthy cats at UK cat shows. *Vet. Rec.* 1994; 135(23): 555-556.

Crandell et al. Development, characterization, and viral susceptibility of a feline (*Felis catus*) renal cell line (CRFK). *In Vitro* 1973; 9(3):176-185.

Dawson et al. Investigation of vaccine reactions and breakdowns after feline calicivirus vaccination. *Vet. Rec.* 1993. 132:346-350.

Dawson et al. Typing of feline calicivirus isolates from different clinical groups by virus neutralisation tests. *Vet. Rec.* 1993. 133:13-17.

Ellis, T. M. Feline respiratory virus carriers in clinically healthy cats. *Australian Vet. J.* 1981; 57(3):115-118.

European Patent No. 0 496 135.

Fastier, L. B. A new feline virus isolated in tissue culture. *Am. J. Vet. Res.* 1957; 18:382-389.

Fields, J. et al., *Nature* 1960. 186:778-780.

Geissler, K. et al. Genetic and antigenic heterogeneity among feline calicivirus isolates from distinct disease manifestations. *Virus Res.* 1997. 48:193-206.

Gobar et al. World Wide Web-based survey of vaccination practices, postvaccinal reactions, and vaccine site-associated sarcomas in cats. *JAVMA* 2002; 220(10):1477-82.

Harbour, D. A. et al. Isolation of feline calicivirus and feline herpesvirus from domestic cats 1980 to 1989. *Vet. Rec.* 1991. 128:77-80.

Hurley et al. Update on feline calicivirus: new trends. *Vet. Clin. Small Anim.* 2003; 33:759-772.

Johnson, R. P. and Povey, R. C. Feline calicivirus infection in kittens borne by cats persistently infected with the virus. *Res. Vet. Sci.* 1984. 31:114-119.

Johnson, R. P. Antigenic change in feline calicivirus during persistent infection. *Can. J. Vet. Res.* 1992. 56:326-330.

Kahn and Gillepsie. Feline viruses. X. Characterization of a newly-isolated picornavirus causing interstitial pneumonia and ulcerative stomatitis in the domestic cat. *Cornell Vet.* 1970. 60:669-683.

Knowles, J. O. et al. Neutralisation patterns among recent British and North American feline calicivirus isolates from different clinical origins. *Vet. Rec.* 1990; 127(6):125-7.

Knowles, J. O. et al. Prevalence of feline calicivirus, feline leukaemia virus and antibodies to FIV in cats with chronic stomatitis. *Vet Rec.* 1989. 124(13):336-8.

Lauritzen A. and Jarrett O. Serological analysis of feline calicivirus isolates from the United States and United Kingdom. *Vet. Microbiol.* 1997. 56:55-63.

Pedersen et al. *Fel. Prac.* 1983. 13:26-35.

Pedersen et al. An isolated epizootic of hemorrhagic-like fever in cats caused by a novel and highly virulent strain of feline calicivirus. *Vet. Microbiol.* 2000; 73:281-300.

Pedersen, N. C. et al. Mechanisms for persistence of acute and chronic feline calicivirus infections in the face of vaccination. *Vet. Microbiol.* 1995. 47:141-156.

*Pharmeuropa* 1996. 8(2).

Poulet et al. Comparison between acute oral/respiratory and chronic stomatitis/gingivitis isolates of feline calicivirus: pathogenicity, antigenic profile and cross-neutralisation studies. *Arch. Virol.* 2000; 145(2):243-261.

Povey C. and Ingersoll J. Cross-protection among feline caliciviruses. *Infection and Immunity* 1975; 11:877-885.

Povey, R. C. and Wilson, M. R. A comparison of inactivated feline viral rhinotracheitis and feline caliciviral disease vaccines with live-modified viral vaccines. *Feline Practice* 1978; 8(3):35-42.

Povey et al. Immunogenicity and safety of an inactivated vaccine for the prevention of rhinotracheitis, caliciviral disease, and panleukopenia in cats. *J. Am. Vet. Med. Assoc.* 1980; 177(4):347-350.

Powell, M. and Newman, M., eds. *Vaccine Design, The Subunit and Adjuvant Approach*, Plenum Press 1995.

Radford, A. D. et al. The use of sequence analysis of a feline calicivirus (FCV) hypervariable region in the epidemiological investigation of FCV related disease and vaccine failures. *Vaccine* 1997. 15:1451-1458.

Radford, A. D et al. Endemic infection of a cat colony with a feline calicivirus closely related to an isolate used in live attenuated vaccines. *Vaccine* 2001. 19(31):4358-62.

Radford, A. D. et al. *Proc. 1st Int. Symp. Caliciviruses ESVV* 1997. 93-99.

Reubel et al. Acute and chronic faucitis of domestic cats. A feline calicivirus-induced disease. *Vet Clin North Am Small Anim Pract.* 1992; 22(6):1347-60.

Schorr-Evans et al. An epizootic of highly virulent feline calicivirus disease in a hospital setting in New England. *J Feline Med Surg.* 2003; 5(4):217-26.

Tohya Y. et al. Characterization of the subunit particles of feline calicivirus. *Nippon Juigaku Zasshi* 1990; 52(5):955-61.

U.S. Pat. No. 2,909,462.
U.S. Pat. No. 5,753,103.
U.S. Pat. No. 6,355,246.
U.S. Pat. No. 6,534,066.

Wardley, R. C. Feline calicivirus carrier state. A study of the host/virus relationship. *Arch. Virol.* 1976. 52(3):243-249.

Weeks, M. L. et al. Sequence analysis of feline caliciviruses isolated from the oral cavity of clinically normal domestic cats (*Felis catus*) in Florida. *Research in Veterinary Science* 2001. 71(3):223-5.

What is claimed is:

1. An immunogenic or vaccine composition comprising a veterinarily acceptable vehicle or excipient and at least one isolated feline calicivirus, wherein the at least one calicivirus is selected from the group consisting of: FCV 431, FCV G1, FCV RMI6, FCV RMI9, FCV 100869, FCV 94580, FCV 33585, FCV 89391, and FCV 88287; and wherein said calicivirus is inactivated.

2. The composition of claim 1 comprising an isolated feline calicivirus strain 100869 deposited at the ATCC under accession number PTA 5930 or comprising an isolated calicivirus strain 431 deposited at the CNCM under the accession number I-2166 and an isolated feline calicivirus strain G1 deposited at the CNCM under accession number I-2167.

3. The composition of claim 2 comprising feline calicivirus strains 431 and G1, and wherein the composition provides an immune response against a hypervirulent feline calicivirus strain, or wherein the composition provides an immune response against a hypervirulent feline calicivirus strain comprising strain 100869.

4. The composition of claim 1 which is a vaccine.

5. The composition of claim 1 additionally comprising an adjuvant.

6. An immunogenic or vaccine composition comprising an isolated feline calicivirus (FCV) strain 431 deposited at the CNCM under accession number I-2166, a veterinarily acceptable vehicle or excipient, and at least one other immunogenic component, which is an attenuated live, an inactivated, a subunit, a recombinant, or a polynucleotide vaccine, which is capable of eliciting an immune response against at least one other feline pathogen.

7. The immunogenic composition of claim 6 additionally comprising an isolated feline calicivirus strain G1 deposited at the CNCM under accession number I-2167.

8. The composition of claim 7, wherein the composition provides an immune response against at least one hypervirulent feline calicivirus.

9. The composition of claim 8, wherein the hypervirulent feline calicivirus is strain 100869.

10. The composition of claim 6 which is a vaccine.

11. The composition of claim 6 additionally comprising an adjuvant.

12. The immunogenic composition of claim 6, wherein the other feline pathogen is selected from the group consisting of feline herpesviruses (FHV), feline leukemia virus (FeLV), feline panleucopenia virus (FPV), feline infectious peritonitis virus (FIPV), feline immunodeficiency virus (FIV), rabies virus, and *Chlamydia*.

13. A kit comprising the immunogenic composition of claim 12.

14. The kit of claim 13, wherein the FCV and the at least one other immunogenic component against the at least one other feline pathogen are packaged separately.

15. A method of immunizing a feline against a hypervirulent feline calicivirus comprising administering an immunogenic or vaccine composition comprising a veterinarily acceptable vehicle or excipient and at least one isolated feline calicivirus, wherein the at least one feline calicivirus is selected from the group consisting of: FCV 431, FCV G1, FCV RMI6, FCV RMI9, FCV 100869, FCV 94580, FCV 33585, FCV 89391, FCV 88287, and equivalents thereto.

16. The method of claim 15, wherein the composition is administered at least twice.

17. The method of claim 15, wherein the FCV is inactivated.

18. The method of claim 15, wherein the composition comprises an isolated feline calicivirus (FCV) strain 431 deposited at the CNCM under accession number I-2166 and an isolated feline calicivirus strain G1 deposited at the CNCM under accession number I-2167 or wherein the composition comprises an isolated feline calicivirus strain 100869 deposited at the ATCC under accession number PTA 5930.

* * * * *